(12) United States Patent
Wu et al.

(10) Patent No.: US 10,696,685 B2
(45) Date of Patent: Jun. 30, 2020

(54) POLYKETIDES, METHODS OF USE AND PREPARATION

(71) Applicant: Universiteit Leiden, Leiden (NL)

(72) Inventors: Changsheng Wu, Leiden (NL); Young-Hae Choi, Leiden (NL); Gilles Philippus van Wezel, Leiden (NL)

(73) Assignee: Universiteit Leiden, Leiden (NL)

( * ) Notice: Subject to any disclaimer, the term of this patent is extended or adjusted under 35 U.S.C. 154(b) by 36 days.

(21) Appl. No.: 15/578,991

(22) PCT Filed: Jun. 3, 2016

(86) PCT No.: PCT/NL2016/050398
§ 371 (c)(1),
(2) Date: Dec. 1, 2017

(87) PCT Pub. No.: WO2016/195495
PCT Pub. Date: Dec. 8, 2016

(65) Prior Publication Data
US 2019/0194217 A1   Jun. 27, 2019

(30) Foreign Application Priority Data

Jun. 3, 2015 (EP) .................................... 15170513

(51) Int. Cl.
| | | |
|---|---|---|
| *C07D 491/107* | (2006.01) |
| *C07D 487/04* | (2006.01) |
| *C07D 491/10* | (2006.01) |
| *A01N 43/38* | (2006.01) |
| *C12P 17/04* | (2006.01) |
| *A61P 31/04* | (2006.01) |
| *A61P 35/00* | (2006.01) |

(52) U.S. Cl.
CPC ......... *C07D 491/107* (2013.01); *A01N 43/38* (2013.01); *C07D 487/04* (2013.01); *C07D 491/10* (2013.01); *C12P 17/04* (2013.01); *A61P 31/04* (2018.01); *A61P 35/00* (2018.01)

(58) Field of Classification Search
CPC ........................ C07D 491/107; C07D 487/04; C07D 491/10; C12P 17/04; A61P 31/04; A61P 35/00
See application file for complete search history.

(56) References Cited

FOREIGN PATENT DOCUMENTS

EP    0372383 A1    6/1990

OTHER PUBLICATIONS

Kharel, M. et al: 11 Angucyclines: Biosynthesis, mode-of-action, new natural products, and synthesis, Natural Product Reports, 2012, vol. 29, No. 2, pp. 264-325.
Rohr, J. et el., Angucycline Group Antibiotics, Natural Product Reports, Royal Society of Chemistry, GB, 1992, vol. 9, pp. 103-137.

*Primary Examiner* — Timothy R Rozof
(74) *Attorney, Agent, or Firm* — Banner & Witcoff, Ltd.

(57) ABSTRACT

The invention is among others concerned with novel polyketides, their method of production, purification and use. The method can entail providing a bacterium that synthesizes the compound.

9 Claims, 23 Drawing Sheets
Specification includes a Sequence Listing.

Figure 1. Rearranged and unrearranged angucyclines from *Streptomyces sp.* QL37. Lugdunomycin (1) is a novel angucycline derivative with unprecedented skeleton. All compounds are biosynthetically related (see Figure 3), whereby 5—7, 10, 11, 16—21, 24, 26—31 with carbon numbering, are novel compounds.
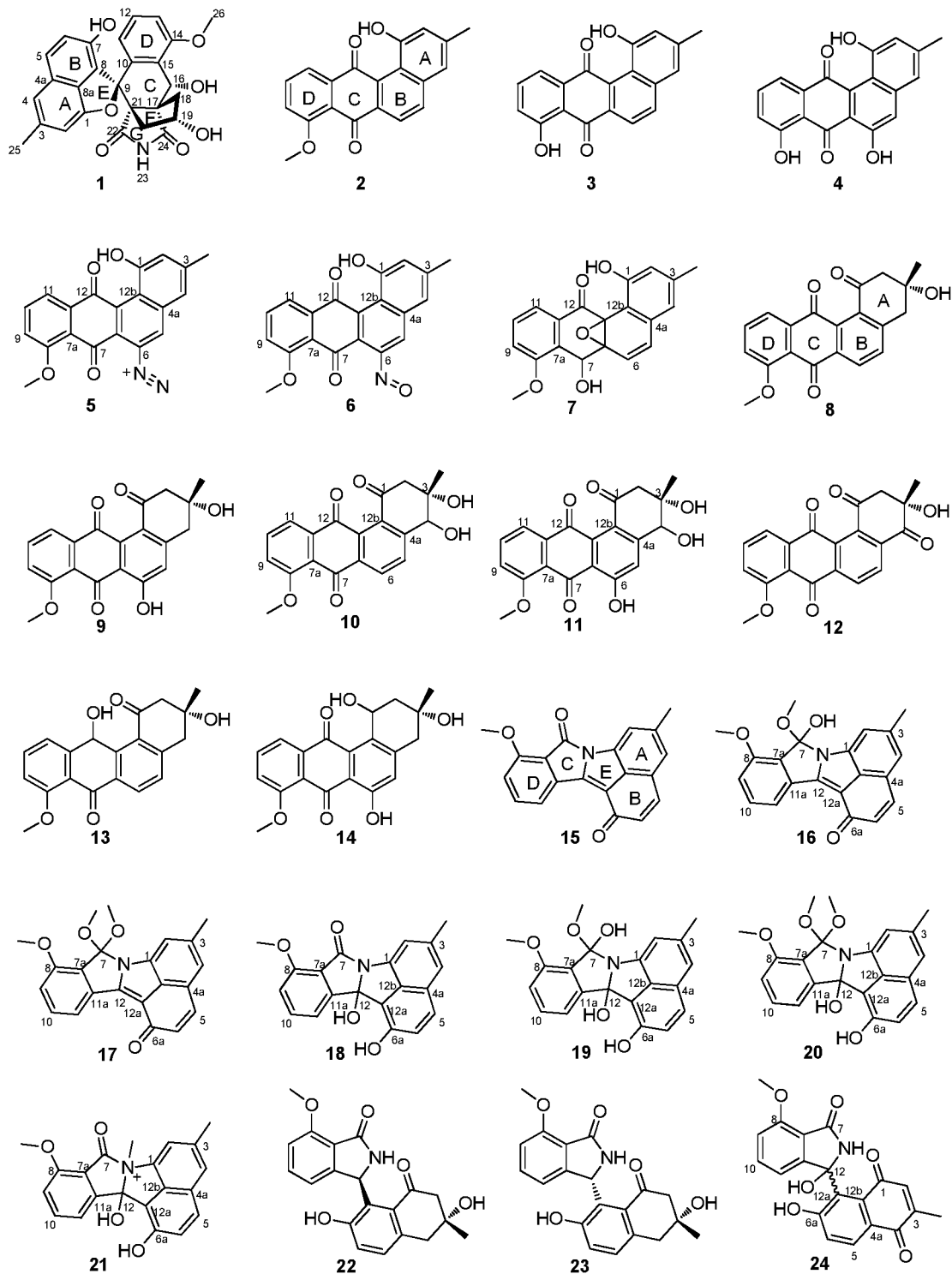

Figure 2. ORTEP drawing of the crystal structure of lugdunomycin (1). The dashed green line represents an intramolecular H-bond between two hydroxyl groups (16-OH and 7-OH). The relative configurations of five chiral centers are 9R, 16R, 17R, 19R, 21S.
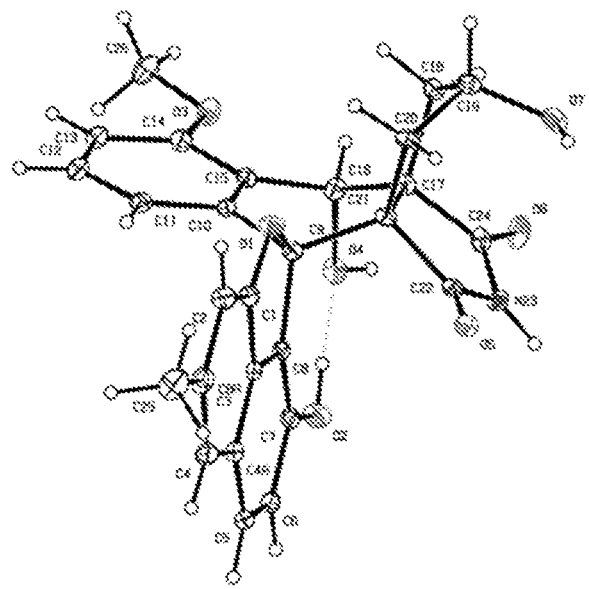

Figure 3. Biosynthetic route to lugdunomycin (1). (A) Organization of the type II PKS gene cluster (*lug*) responsible for lugdunomycin (1) biosynthesis in *Streptomyces* sp. QL37. Annotations of respective gene are displayed in Table 2, and genes are depicted in five different colors according to general functions. (B) Expected synthesis route for lugdunomycin and other angucycline antibiotics presented in Figure 1. All of the compounds in Figure 1 are biosynthetically related. Lugdunomycin likely originates from Baeyer–Villiger oxidative cleavage at the D ring of compound 2, which is presumably executed by oxygenase *lugOII*. The reactive aldehyde group is thereby non-enzymatically coupled with one molecule of 3-hydroxypathalimde through Diels–Alder [4+2] cycloaddition, followed by spontaneous domino reactions, involving a sequence of Michael addition of α,β-conjugated enone with nucleophile reagent $H_2O$, nucleophilic Favorskii rearrangement, and release of one molecule of $CO_2$.

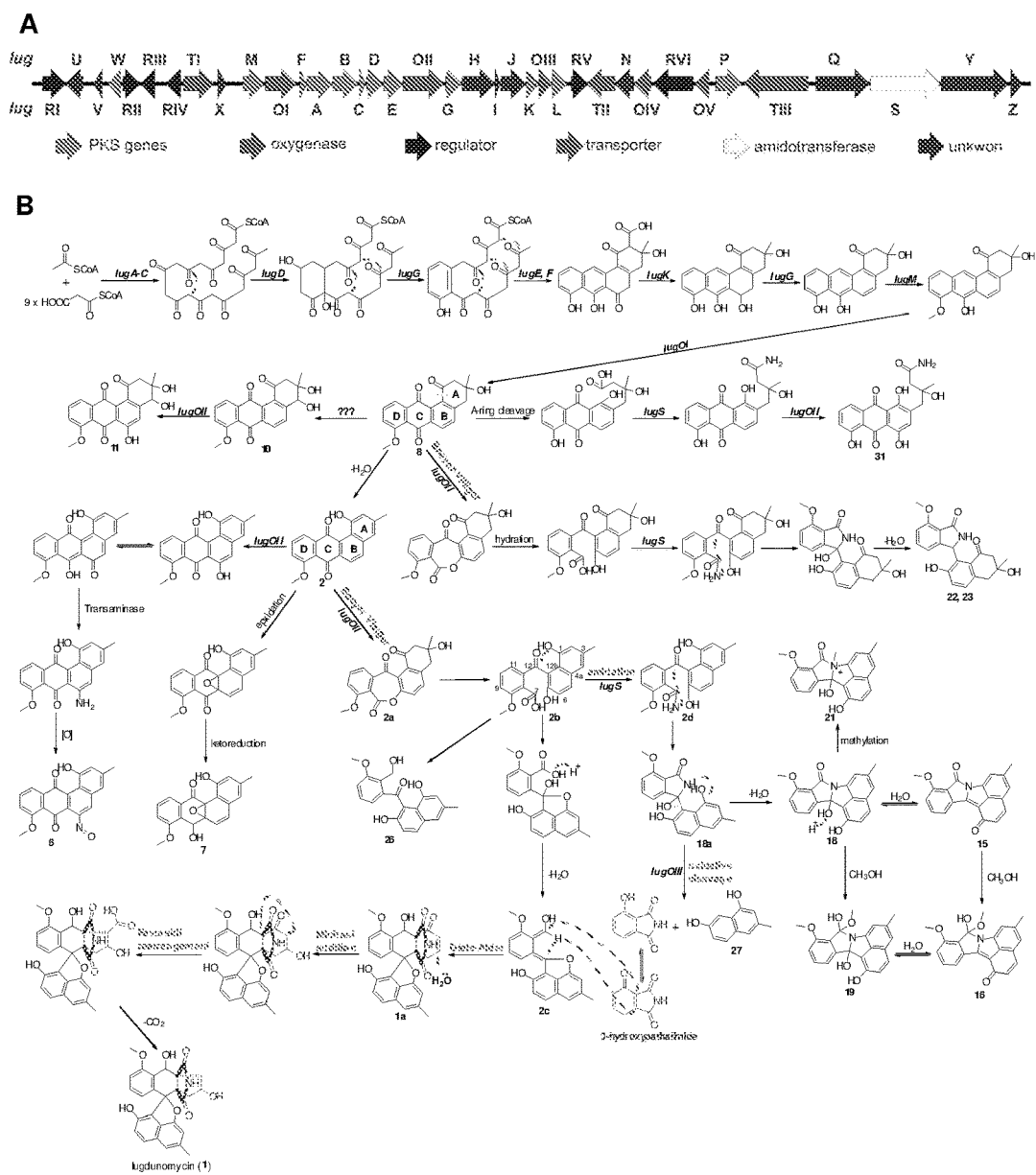

Figure 4. HPLC-UV profiling (detected at 254 nm) confirmed *lug* gene cluster is responsible for angucycline biosynthesis. The angucycline/ones (such as 8 and 13) were abolished in the minimal PKS genes *lugA—C* null mutant.
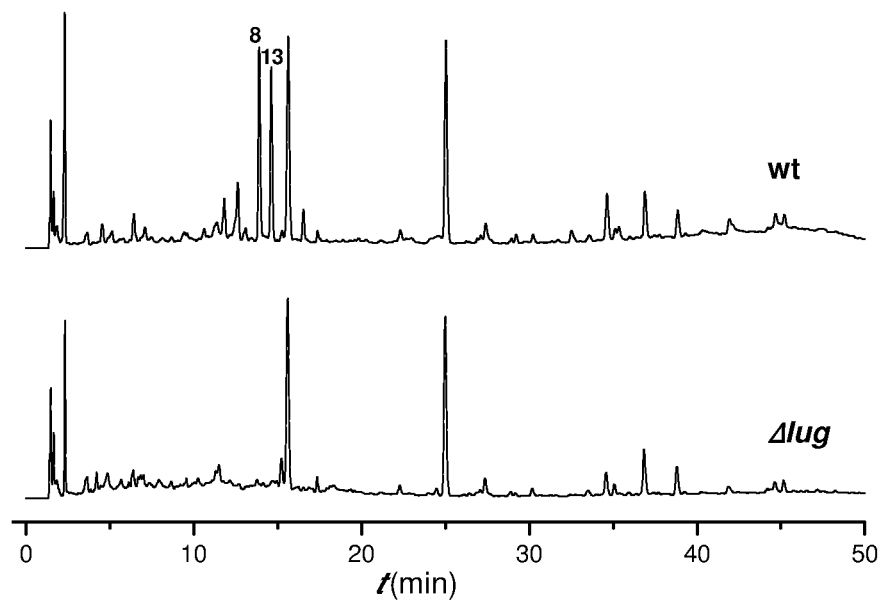

Figure 5. Schematic illumination of potential chemoenzymatic approach to synthesize lugdunomycin variants.
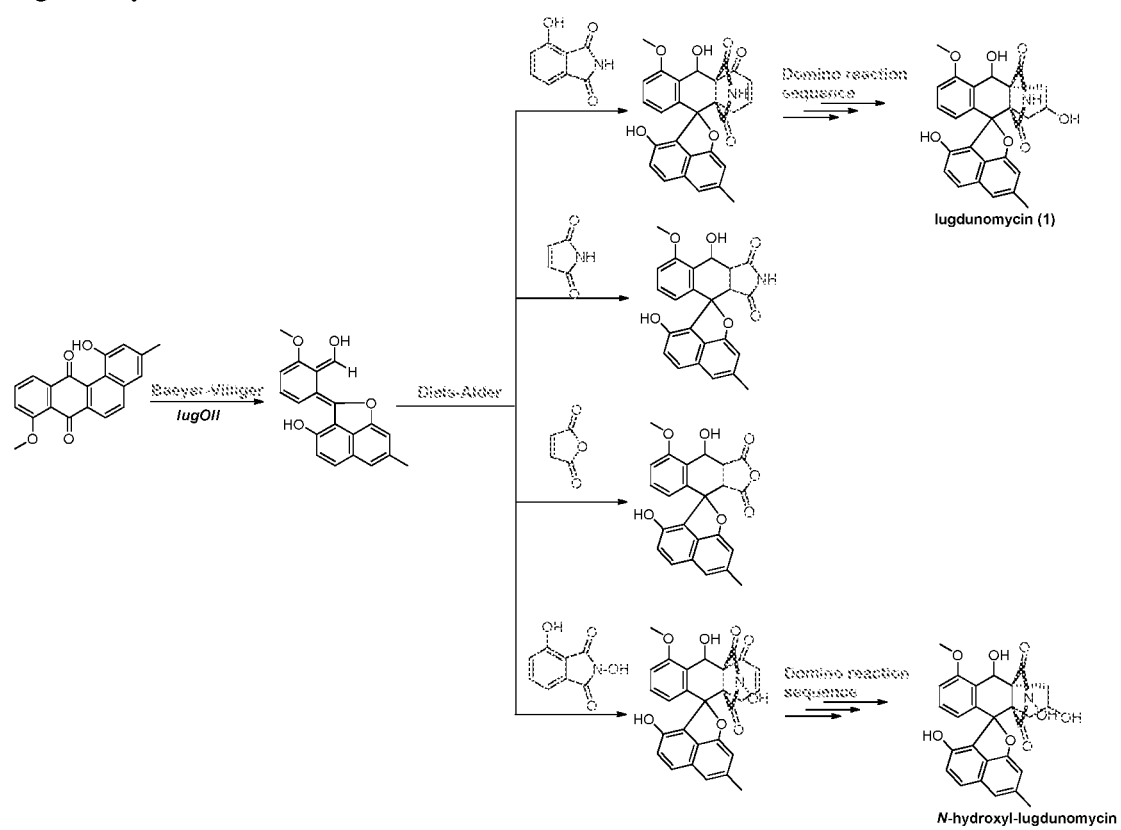

Figure 6. Preliminary antimicrobial activity test of lugdunomycin (1) and selected angucyclines. Numbering on the paper disc corresponds to the numbering of the compounds as presented in figure 1, e.g. 1 stands for lugdunomycin, 6 for the novel angucycline derivative with nitroso group. Lugdunomycin (1) showed inhibition efficacy against Gram-positive bacterium *Bacillus subtilis* (A), but not against Gram-negative *Escherichia coli* JM 109 (B); All the selected angucylines simultaneously inhibited the growth of both *Bacillus subtilis* (C) and *Escherichia coli* JM109 (D). Note: compounds 8 and 9 were obtained as a mixture, which were tested activity together; AMP: postitive control, ampicillin.

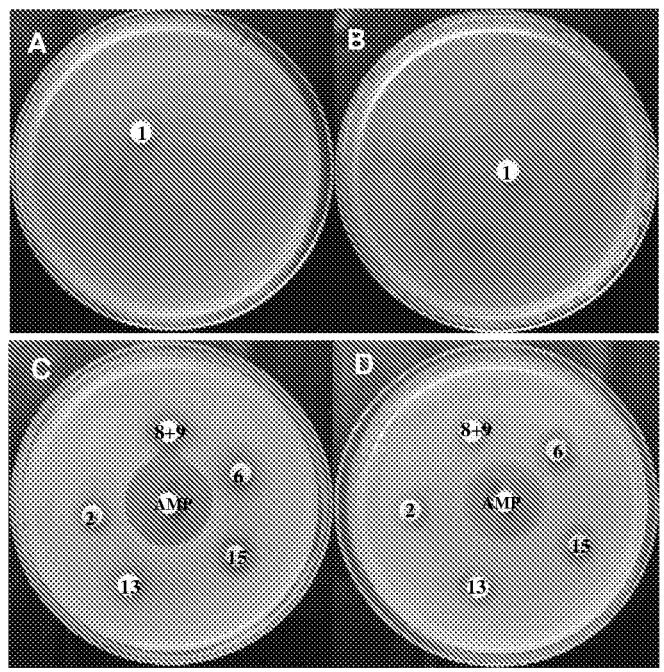

Figure 7. A. Image of *Streptomyces* sp. QL37 grown on SFM agar (left) and a stereo micrograph of a single colony (right). The diameter of the agar plate was 90 mm, the diameter of the colony on the right 5 mm. B. Thin layer chromatography (TLC) analysis of the metabolome of QL37 and six randomly chosen actionomycetes from our strain collection as comparison, all grown under six different culture conditions. Crude extracts were dissolved in ethyl acetate to a concentration of 20 mg/ml, and solutions were spotted on a TLC plate using a capillary. TLC was migrated by a solvent system of chloroform/methanol (10:1), visualized under UV at 254 nm (top), and further stained with anisaldehyde/sulfuric acid reagent by heating (bottom). Dash boxed lanes are strain QL37 grown on solid Minimal Medium (MM) agar, which gave the most spots corresponding to secondary metabolites and this suggested it was a promising strain for systematic and detailed chemical investigation.

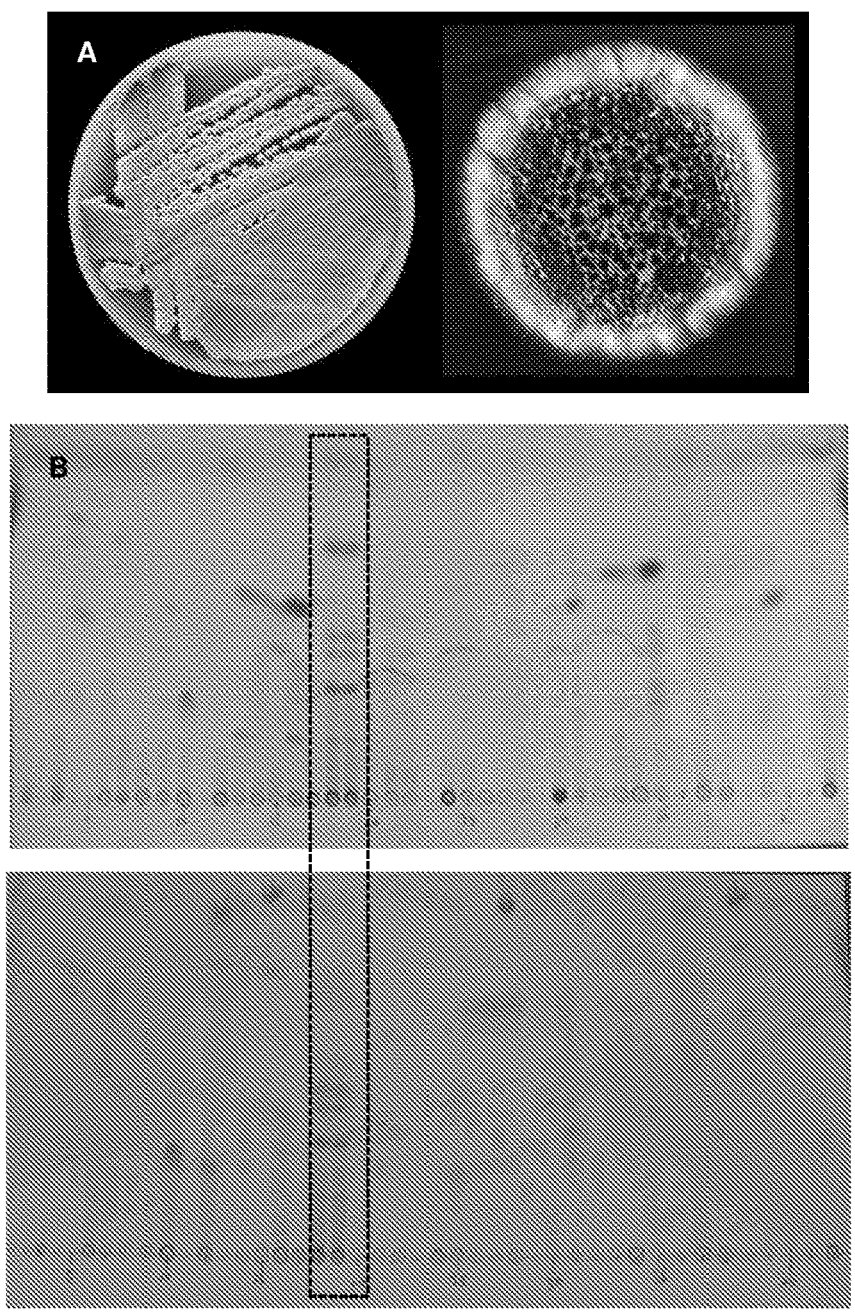

Figure 8. Antimicrobial activity assay of ethyl acetate extracts of the seven actinomycetes analysed by TLC in Figure 7B, and grown under six different conditions. For each plate, from top to bottom and from left to right: (1) NMMP with mannitol (0.5% w/v) and glycerol (1% w/v); (2) NMMP pH 10; (3) Solid MM; (4) NMMP with 0.5% (w/v) Bacto yeast extract; (5) NMMP with 1% (w/v) Bacto peptone; (6) NMMP with 1% (w/v) Soy Flour. An agar diffusion assay was conducted by using *Bacillus subtilis* as indicator strain. Crude extracts were dissolved in ethyl acetate to 20 mg/ml, and 20 µl was pipetted onto a paper disc to determine the antibacterial activity. QL37 (highlighted with a dashed circle) showed better antimicrobial activity in solid MM than all modified liquid NMMP culture media and this was therefore the preferred media.

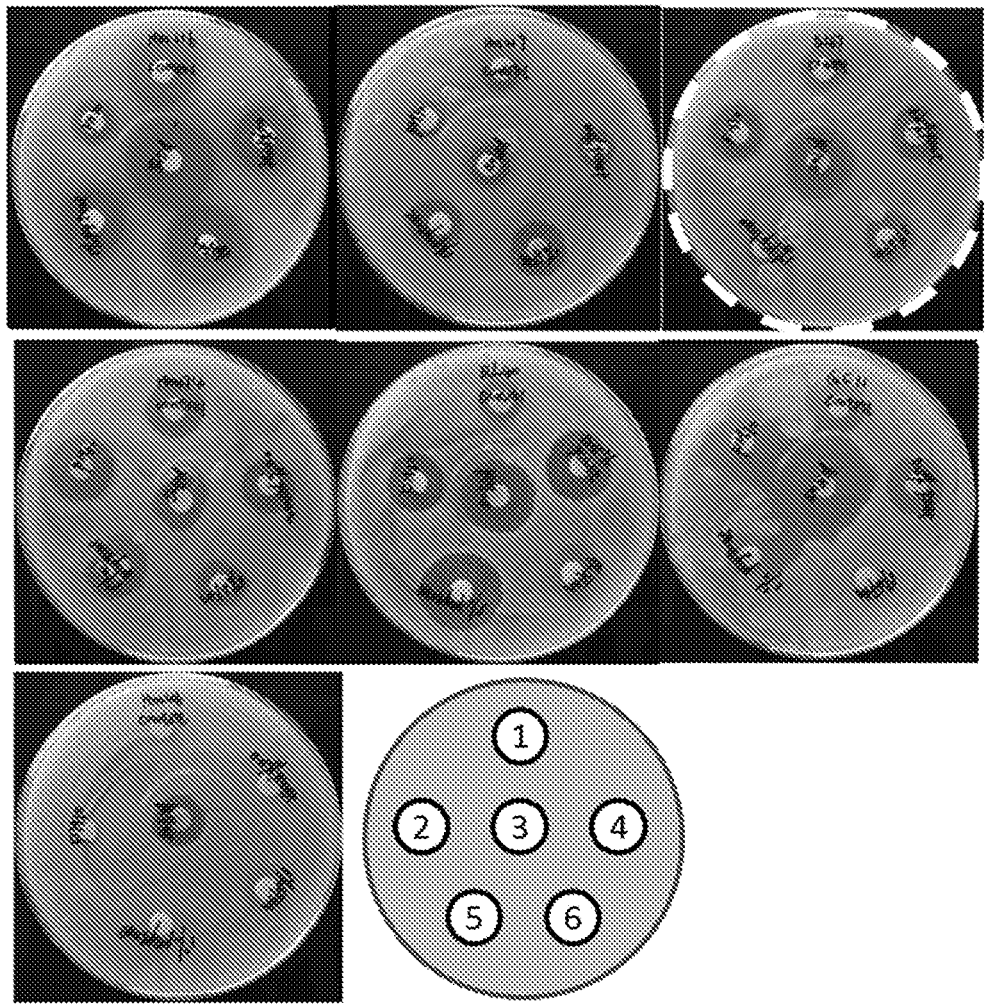

Figure 9. Detection of Lugdunomycin (1) by thin layer chromatography (TLC). TLC was migrated by a solvent system of chloroform/methanol (10:1, $R_f$ = 0.26). Lugdunomycin gave a dark spot under UV at 254 nm (left), and a distinctive blue color when further stained with anisaldehyde/sulfuric acid reagent by heating (right).
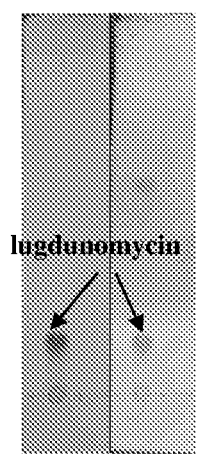

Figure 10. Racemic structure of lugdunomycin, showing structures of lugdunomycin (+)-1 and (−)-1
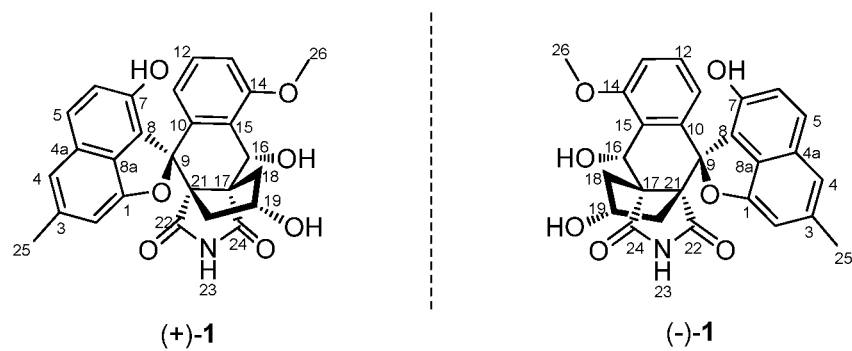
(+)-1                    (-)-1

Figure 11. 2D NMR correlations of lugdunomycin (1) and selected new angucyclines 5–7, 10, 11, 16, 18, 19, 22, 27, and 31. Displayed are HMBC ( ) and COSY (—) correlations for determination of planar structure.
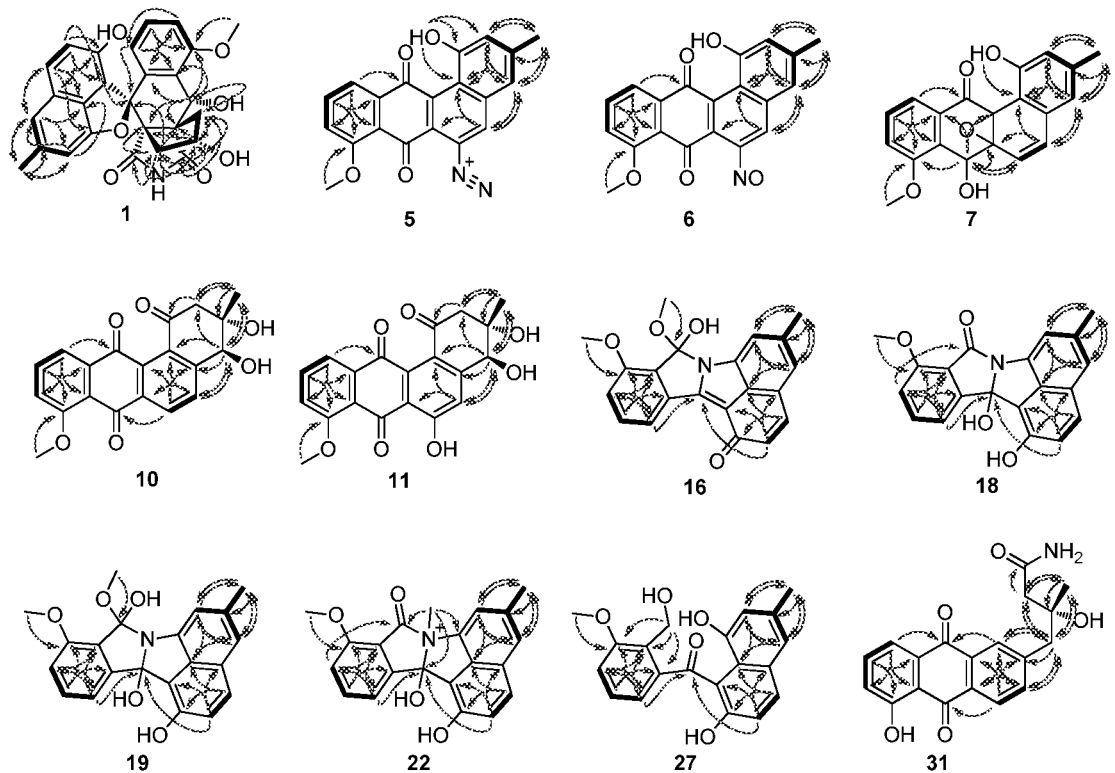

Figure 12. Spectral list of lugdunomycin (1).

S1. $^1$H NMR spectrum (600 MHz) of lugdunomycin (1) in CD$_3$OD.
S2. APT spectrum (600 MHz) of lugdunomycin (1) in CD$_3$OD.
S3. HSQC spectrum (600 MHz) of lugdunomycin (1) in CD$_3$OD.
S4. HMBC spectrum (600 MHz) of lugdunomycin (1) in CD$_3$OD.
S5. $^1$H-$^1$H COSY spectrum (600 MHz) of lugdunomycin (1) in CD$_3$OD.
S6. $^1$H-$^1$H NOSEY spectrum (600 MHz) of lugdunomycin (1) in CD$_3$OD.
S7. HRESIMS spectrum of lugdunomycin (1).
S8. IR spectrum of lugdunomycin (1).
S9. UV spectrum of lugdunomycin (1).
S10. CD spectrum of lugdunomycin (1).

S1. ¹H NMR spectrum (600 MHz) of lugdunomycin (1) in CD$_3$OD.

S2. ¹³C NMR spectrum (150 MHz) of lugdunomycin (1) in CD$_3$OD.

Figure 12 (Cont.)
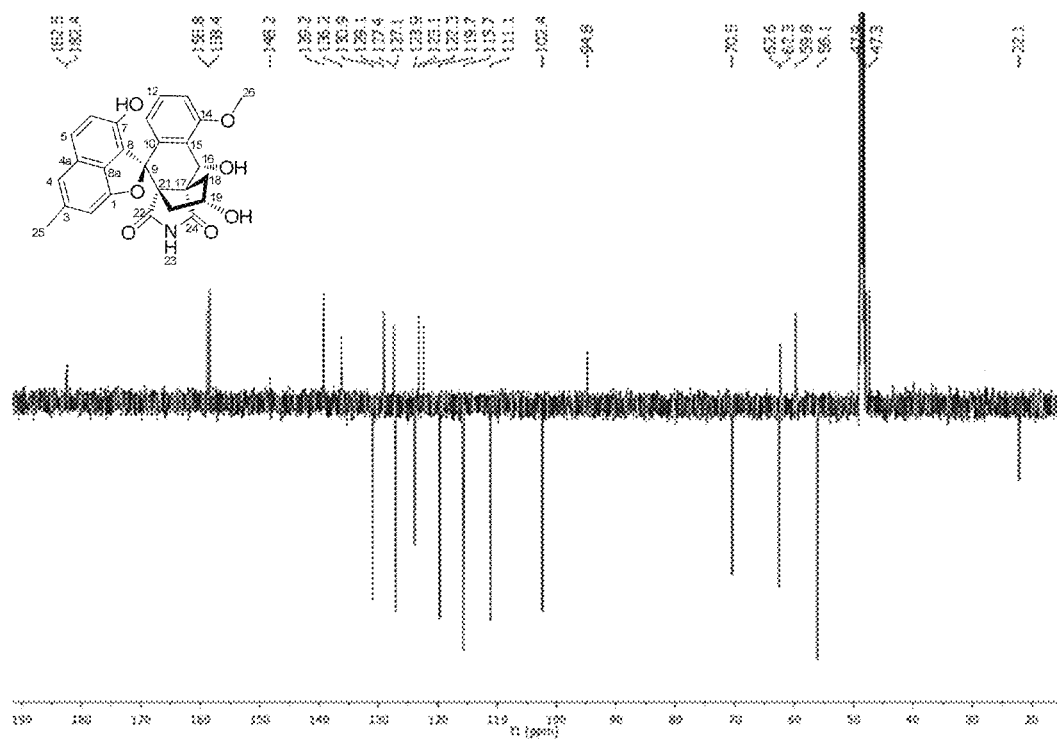
S3. HSQC spectrum (600 MHz) of lugdunomycin (1) in $CD_3OD$.
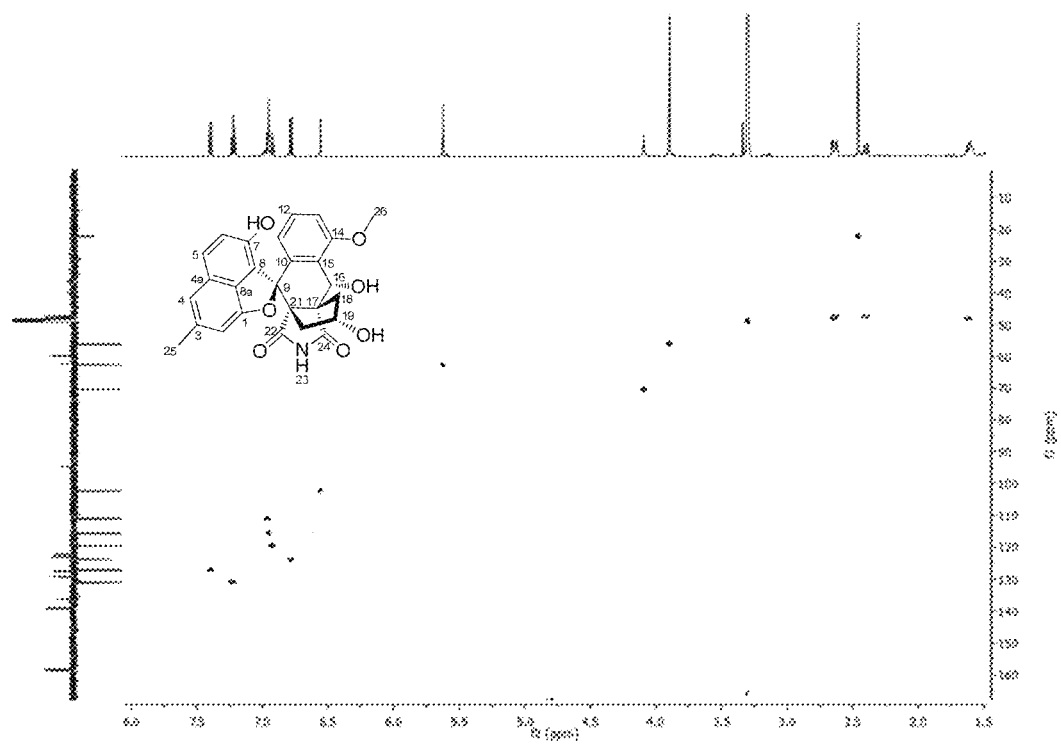

Figure 12 (Cont.)
S4. HMBC spectrum (600 MHz) of lugdunomycin (1) in CD₃OD.
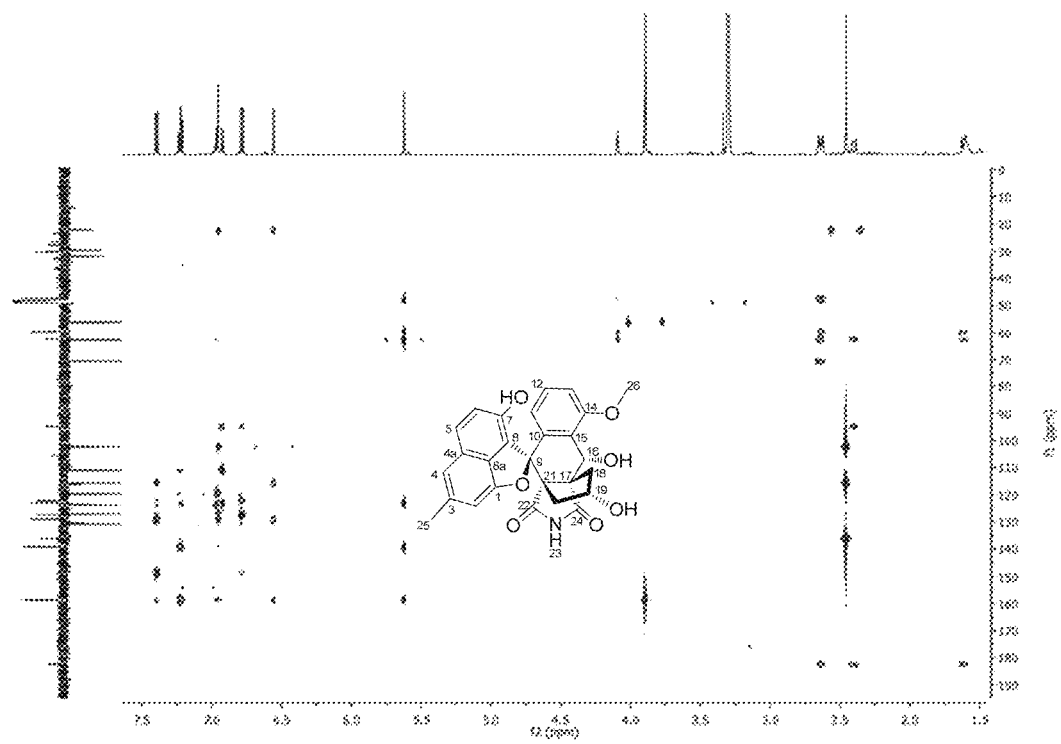
S5. ¹H-¹H COSY spectrum (600 MHz) of lugdunomycin (1) in CD₃OD.
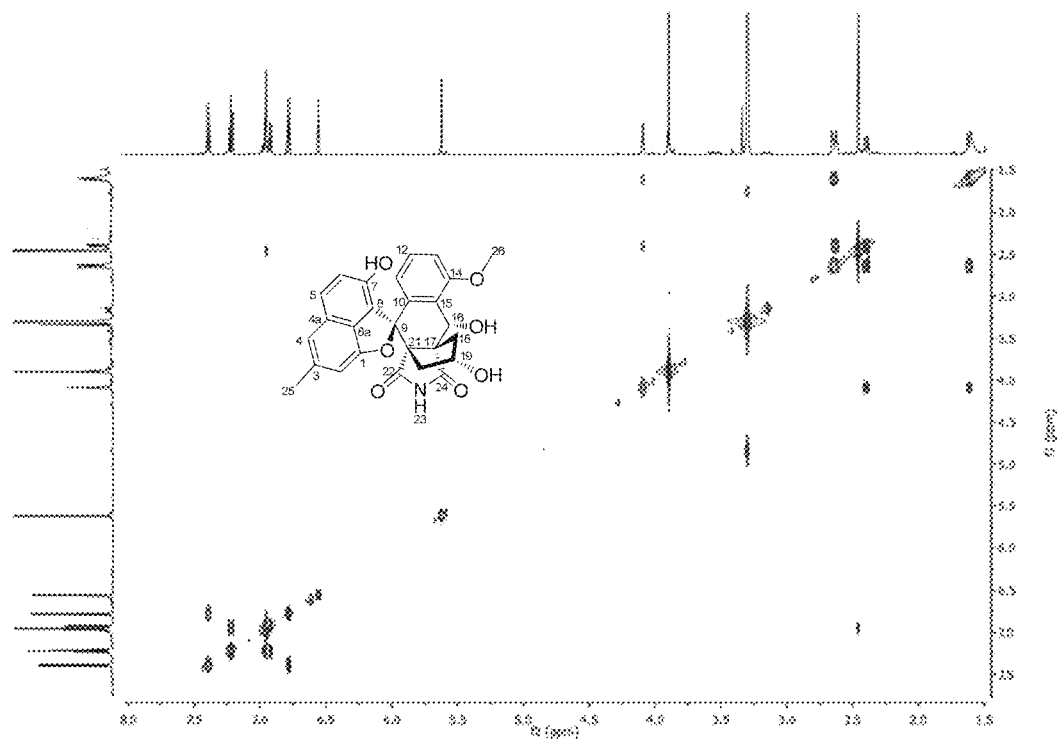

S6. ¹H-¹H NOSEY spectrum (600 MHz) of lugdunomycin (1) in CD₃OD.

S5. HRESIMS spectrum of lugdunomycin (1).

S6. IR spectrum of lugdunomycin (1).

Figure 12 (Cont.)
S7. UV spectrum of lugdunomycin (1).
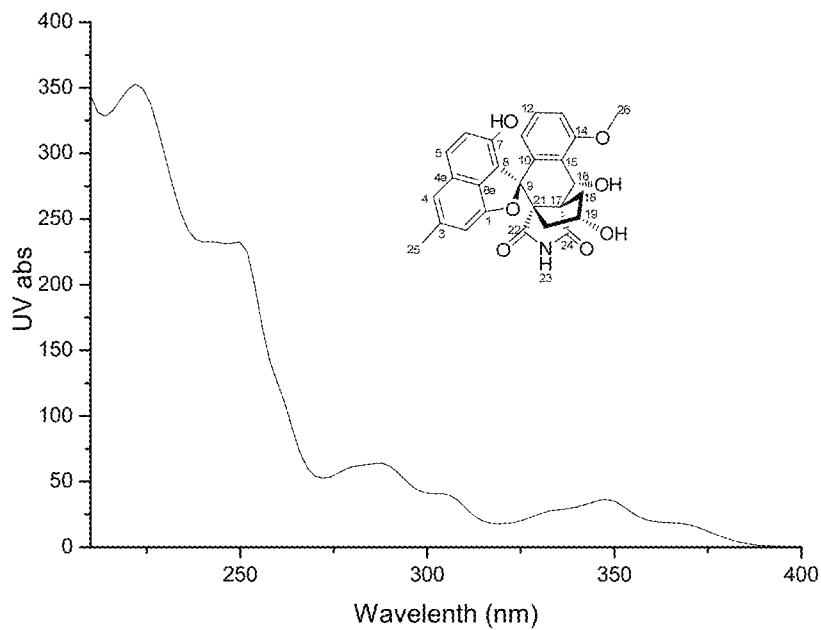
S9. CD spectrum of lugdunomycin (1).
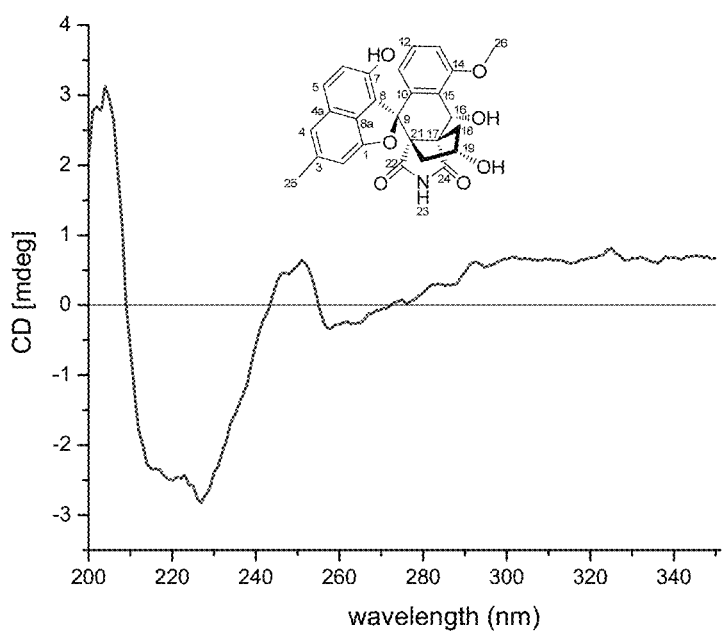

Figure 13:
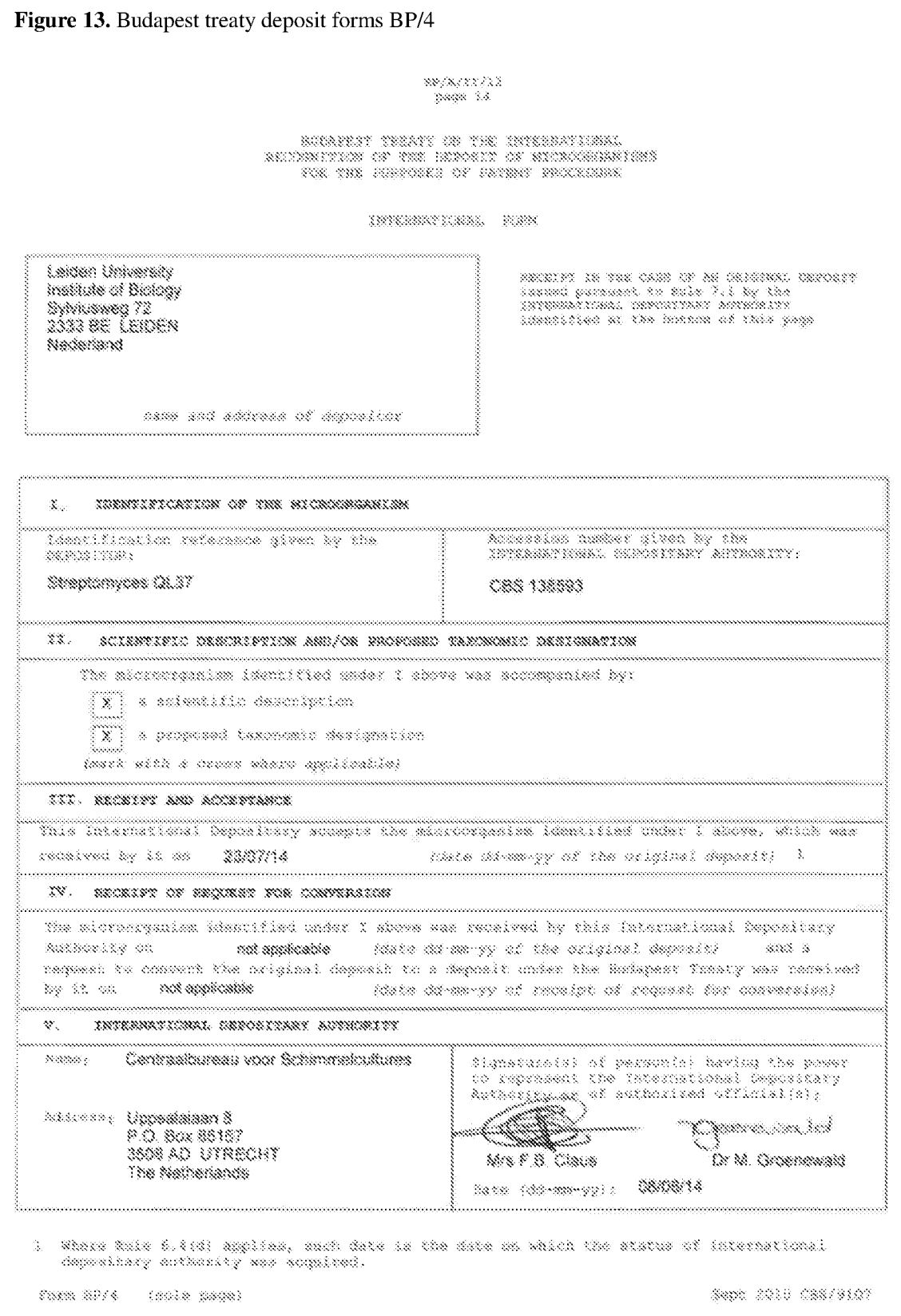
Figure 13:
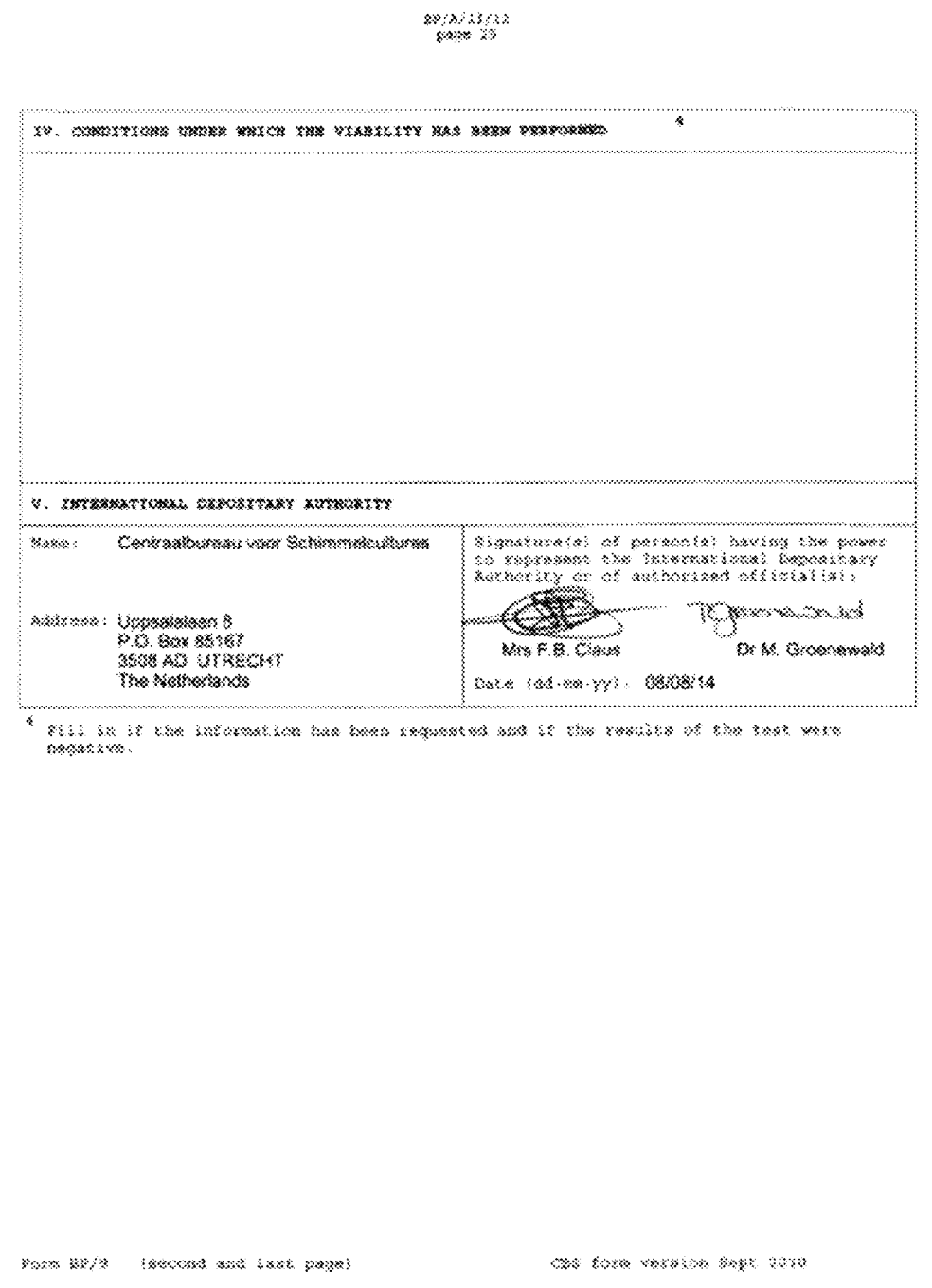

Figure 13. Budapest treaty deposit forms BP/4

POLYKETIDES, METHODS OF USE AND PREPARATION

SEQUENCE LISTING

The instant application contains a Sequence Listing which has been submitted electronically in ASCII format and is hereby incorporated by reference in its entirety. Said ASCII copy, created on Sep. 17, 2018, is named P106702US00_ST25.txt and is 4,000 bytes in size.

The invention relates to novel polyketides, their production and use. The invention in particular relates to polyketides that can be produced by bacteria. The novel compounds are typically biologically active.

The compounds are a subgroup of the large family of polyketides and in particular the angucyclines/angucyclinones. The angucyclines/angucyclinones are characterized by diverse biological activities. Compounds of the group are known to have antitumor activity, antibacterial activity, enzyme inhibitory activity and other activities.

The angucycline/angucyclinone group is the largest group of type II polyketides (PKS)-engineered natural products. The group is rich in biological activities and chemical scaffolds. Many of the natural compounds or derivatives thereof can be produced synthetically. The synthesis strategies vary and can involve Diels-Alder reactions, nucleophilic additions, electrophilic additions, transition-metal mediated cross-couplings and intramolecular cyclizations to generate angucycline/angucyclinone frames. Biosynthetic studies were particularly intriguing when unusual framework rearrangements by post-PKS tailoring oxidoreductases occurred, or when unusual glycosylation reactions were involved in decorating the benz[a]anthracene-derived cores.

The group of angucycline/angucyclinones/angucyclinones described in the present invention are herein referred to as the lugdunomycin group, the lugdunomycines. Lugdunomycins have a new chemical scaffold that does not compare to that of other angucycline-type antibiotics. Some members of the group of lugdunomycines were identified as products of Streptomyces species QL37 (CBS 138593; see FIG. 1).

The rapid increase in antibiotic resistance urges the revival of antimicrobial drug discovery efforts. Here we describe the identification and synthesis of lugdunomycines (see FIG. 1 and formula's 1-4 below) with unprecedented chemical scaffold produced by Streptomyces species QL37. Identification of the biosynthetic gene cluster revealed that in fact these molecules are based on angucycline/angucyclinone-type polyketides. The biosynthesis of the heptacyclic lugdunomycines involves an uncommon oxidative opening in a quinone ring of a well-known angucycline precursor. The generated oxidative intermediate was coupled with one molecule of 3-hydroxypathalimde through Diels-Alder [4+2] cycloaddition, followed by spontaneous domino reactions, involving a sequence of Michael addition of α,β-conjugated enone with nucleophile reagent $H_2O$, nucleophilic Favorskii rearrangement, and release of one molecule of $CO_2$.

The planar structure of lugdunomycin (1) was elucidated by interpretation of the NMR spectra and verified by X-ray diffraction. The described lugdunomycines are biologically active. Members of the group can inhibit the growth of one or more Gram-positive and one or more Gram-negative bacteria, inhibit the growth of one or more fungi and/or inhibit the growth of or more types of eukaryotic cells.

The invention provides a compound of formula 1 or formula 2

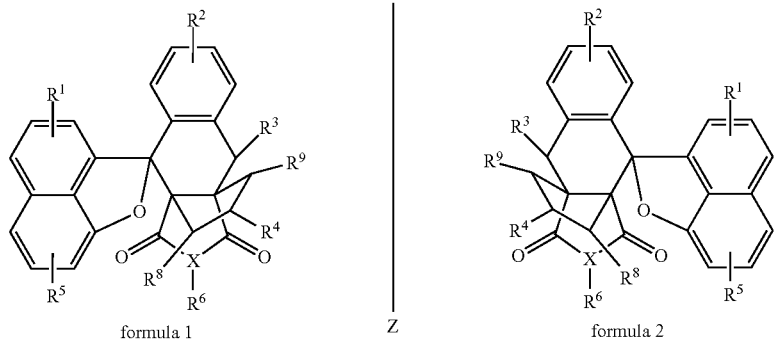

wherein X can be an N, O or S atom;

wherein $R^1$, $R^2$, $R^3$, $R^4$, $R^5$, $R^8$, and $R^9$ are each independently aryl, acyl, methyl, $C_2$-$C_{10}$ alkyl, $C_3$-$C_6$ cycloalkyl, monosaccharide, polysaccharide with 2-5 consecutive saccharide rings, O, OH, N, NH, S, SH, hydrogen or an ether of the general formula —O—$R^7$, wherein $R^7$ is methyl, ethyl or propyl; and $R^6$ is aryl, acyl, methyl, $C_2$-$C_{10}$ alkyl, $C_3$-$C_6$ cycloalkyl, monosaccharide, polysaccharide with 2-5 consecutive saccharide rings, O, OH, or hydrogen.

Formula 1 and formula 2 are nonsuperposable mirror images of each other (the mirror plane is identified by line Z). Each compound of formula 1 has an enantiomer of identical chemical composition of formula 2.

The radicals $R^1$, $R^2$ and $R^6$ can replace any of the hydrogens associated to a carbon atom of the respective benzene rings. In a preferred embodiment the position of $R^1$ in a compound of formula 1 or formula 2 is the position indicated for $R^1$ in the compound of formula 3 or formula 4 presented herein below. In a preferred embodiment the position of $R^2$ in a compound of formula 1 or formula 2 is the position indicated for $R^2$ in the compound of formula 3 or formula 4 presented herein below. In a preferred embodiment the position of $R^5$ in a compound of formula 1 or formula 2 is the position indicated for $R^5$ in the compound of formula 3 or formula 4 presented herein below.

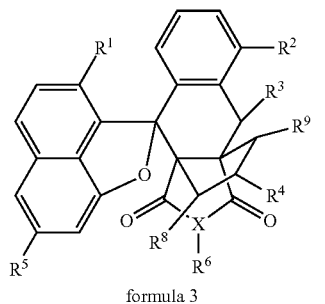 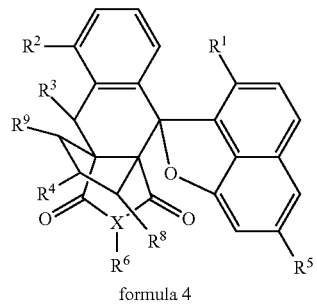

formula 3                    Z                    formula 4

In a particularly preferred embodiment the invention provides a compound of formula 3 or formula 4, wherein $R^1$, $R^2$, $R^3$, $R^4$, $R^5$, $R^8$, and $R^9$ are each independently aryl, acyl, methyl, $C_2$-$C_{10}$ alkyl, $C_3$-$C_6$ cycloalkyl, monosaccharide, polysaccharide with 2-5 consecutive saccharide rings, O, OH, N, NH, S, SH, hydrogen or an ether of the general formula —O—$R^7$, wherein $R^7$ is methyl, ethyl or propyl; and $R^6$ is aryl, acyl, methyl, $C_2$-$C_{10}$ alkyl, $C_3$-$C_6$ cycloalkyl, monosaccharide, polysaccharide with 2-5 consecutive saccharide rings, O, OH, or hydrogen.

$R^1$ in a formula of the invention is preferably methyl, $C_2$-$C_{10}$ alkyl, monosaccharide, polysaccharide with 2-5 consecutive saccharide rings, O, OH, N, NH, S, SH, hydrogen or an ether of the general formula —O—$R^7$, wherein $R^7$ is methyl, ethyl or propyl. $R^1$ is preferably methyl, $C_2$-$C_5$ alkyl, monosaccharide, polysaccharide with 2-5 consecutive saccharide rings, O, OH, or an ether of the general formula —O—$R^7$, wherein $R^7$ is methyl, ethyl or propyl. $R^1$ is preferably O, OH, or an ether of the general formula —O—$R^7$, wherein $R^7$ is methyl, ethyl or propyl. In a particularly preferred embodiment $R^1$ is OH.

$R^2$ in a formula of the invention is preferably methyl, $C_2$-$C_{10}$ alkyl, monosaccharide, polysaccharide with 2-5 consecutive saccharide rings, O, OH, N, NH, S, SH, hydrogen or an ether of the general formula —O—$R^7$, wherein $R^7$ is methyl, ethyl or propyl. $R^2$ is preferably methyl, $C_2$-$C_5$ alkyl, monosaccharide, polysaccharide with 2-5 consecutive saccharide rings, O, OH, or an ether of the general formula —O—$R^7$, wherein $R^7$ is methyl, ethyl or propyl. $R^2$ is preferably O, OH, or an ether of the general formula —O—$R^7$, wherein $R^7$ is methyl, ethyl or propyl. In a particularly preferred embodiment $R^2$ is an ether of the general formula —O—$R^7$, wherein $R^7$ is methyl, ethyl or propyl. In a particularly preferred embodiment $R^2$ is an ether of the general formula —O—$R^7$, wherein $R^7$ is methyl.

$R^3$ in a formula of the invention is preferably methyl, $C_2$-$C_{10}$ alkyl, monosaccharide, polysaccharide with 2-5 consecutive saccharide rings, O, OH, N, NH, S, SH, hydrogen or an ether of the general formula —O—$R^7$, wherein $R^7$ is methyl, ethyl or propyl. $R^3$ is preferably methyl, $C_2$-$C_5$ alkyl, monosaccharide, polysaccharide with 2-5 consecutive saccharide rings, O, OH, or an ether of the general formula —O—$R^7$, wherein $R^7$ is methyl, ethyl or propyl. $R^3$ is preferably O, OH, or an ether of the general formula —O—$R^7$, wherein $R^7$ is methyl, ethyl or propyl. In a particularly preferred embodiment $R^3$ is OH.

$R^4$ in a formula of the invention is preferably methyl, $C_2$-$C_{10}$ alkyl, monosaccharide, polysaccharide with 2-5 consecutive saccharide rings, O, OH, N, NH, S, SH, hydrogen or an ether of the general formula —O—$R^7$, wherein $R^7$ is methyl, ethyl or propyl. $R^4$ is preferably methyl, $C_2$-$C_5$ alkyl, monosaccharide, polysaccharide with 2-5 consecutive saccharide rings, O, OH, or an ether of the general formula —O—$R^7$, wherein $R^7$ is methyl, ethyl or propyl. $R^4$ is preferably O, OH, or an ether of the general formula —O—$R^7$, wherein $R^7$ is methyl, ethyl or propyl. In a particularly preferred embodiment $R^4$ is OH.

R5 in a formula of the invention is preferably methyl, $C_2$-$C_{10}$ alkyl, monosaccharide, polysaccharide with 2-5 consecutive saccharide rings, O, OH, N, NH, S, SH, hydrogen or an ether of the general formula —O—$R^7$, wherein $R^7$ is methyl, ethyl or propyl. $R^5$ is preferably methyl, $C_2$-$C_5$ alkyl, monosaccharide, polysaccharide with 2-5 consecutive saccharide rings, O, OH, or an ether of the general formula —O—$R^7$, wherein $R^7$ is methyl, ethyl or propyl. $R^5$ is preferably O, OH, or an ether of the general formula —O—$R^7$, wherein $R^7$ is methyl, ethyl or propyl. In a particularly preferred embodiment $R^5$ is methyl.

$R^6$ in a formula of the invention is preferably is methyl, $C_2$-$C_{10}$ alkyl, monosaccharide, polysaccharide with 2-5 consecutive saccharide rings, O, OH, or hydrogen. $R^6$ is preferably methyl, $C_2$-$C_5$ alkyl, O, OH, or hydrogen. $R^6$ is preferably O, OH or hydrogen. In particularly preferred embodiment $R^6$ is hydrogen.

$R^8$ in a formula of the invention is preferably methyl, $C_2$-$C_{10}$ alkyl, monosaccharide, polysaccharide with 2-5 consecutive saccharide rings, O, OH, N, NH, S, SH, hydrogen or an ether of the general formula —O—$R^7$, wherein $R^7$ is methyl, ethyl or propyl. $R^8$ is preferably methyl, $C_2$-$C_5$ alkyl, monosaccharide, polysaccharide with 2-5 consecutive saccharide rings, O, OH, or an ether of the general formula —O—$R^7$, wherein $R^7$ is methyl, ethyl or propyl. $R^8$ is preferably O, OH, or an ether of the general formula —O—$R^7$, wherein $R^7$ is methyl, ethyl or propyl. In a particularly preferred embodiment $R^8$ is OH.

$R^9$ in a formula of the invention is preferably methyl, $C_2$-$C_{10}$ alkyl, monosaccharide, polysaccharide with 2-5 consecutive saccharide rings, O, OH, N, NH, S, SH, hydrogen or an ether of the general formula —O—$R^7$, wherein $R^7$ is methyl, ethyl or propyl. $R^9$ is preferably methyl, $C_2$-$C_5$ alkyl, monosaccharide, polysaccharide with 2-5 consecutive saccharide rings, O, OH, or an ether of the general formula —O—$R^7$, wherein $R^7$ is methyl, ethyl or propyl. $R^9$ is preferably O, OH, or an ether of the general formula —O—$R^7$, wherein $R^7$ is methyl, ethyl or propyl. In a particularly preferred embodiment $R^9$ is OH.

The orientation of bonds in the lugdunomycin is preferably the orientation as indicated formula 5. Where an orientation is not specifically indicated the orientation is in the same plane as the benzene ring plane to which the bond is directly attached, or the orientation of the bond can be any of the possible orientations in the structure. Formula 5 indicates a preferred orientation of bonds in a compound of formula 1 or formula 3. The corresponding preferred orientations in an enantiomer of formula 2 or formula 4 is obtained by providing the mirror image of the compound of formula 5 over the plane indicated by line Z, as shown in formula 6.

The invention further provides a method for the treatment of an individual that is infected by a pathogen, or at risk of being infected, the method comprising administering a dose of a compound of formula 1 and/or formula 2 to the individual in need thereof. The compound or composition of the invention is preferably administered in one or more

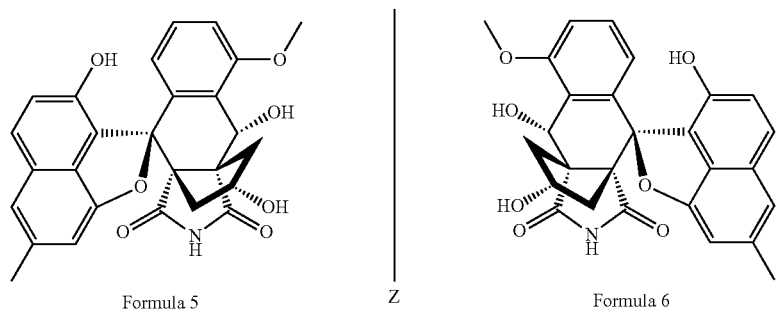

Formula 5    Z    Formula 6

The invention further provides a composition comprising two or more compounds of formula 1-4. In a preferred embodiment at least two of said two or more compounds are enantiomers of each other. One of the enantiomers in the composition is preferably a compound of formula 1 (preferably formula 3), and the other of said enantiomers is preferably a compound of formula 2 (preferably formula 4). In a preferred embodiment the invention provides a composition comprising at least two compounds of formula 1-4 wherein a first compound is a compound of formula 1 and at least a second (another) compound of formula 1-4 is an enantiomer of said first compound. Said second compound is preferably a compound of formula 2. Said compound of formula 1 is preferably a compound of formula 3 and said compound of formula 2 is preferably a compound of formula 4. The orientation of the bonds is preferably the orientation of formula 5 (for compounds of formula 1 and/or 3; and/or the mirror image with respect to the plane identified by line Z, for compounds of formula 2 and/or 4.

X in the 5-ring to which group $R^6$ is attached can be a N, O or S atom. In a preferred embodiment X is an N or O atom. In a preferred embodiment X is an N atom.

The invention further provides a compound or a composition of the invention for use in inhibiting growth of a micro-organism, an animal cell or a virus. The micro-organism is preferably a bacterium, an archea, a fungus, or a protozoan, presently classified as excavata, amoeba, chromalveolata and rhizaria. The bacterium is preferably a Gram-positive or a Gram-negative bacterium.

Preferred Gram-negative bacteria are members of the genus *Acinetobacter, Escherichia, Klebsiella* or *Pseudomonas*. Preferred Gram-positive bacteria are members of the genus *Bacillus, Clostridium, Enterococcus, Mycobacterium, Staphylococcus* or *Streptococcus*. In another preferred embodiment the micro-organism is a fungus.

The micro-organism is preferably a pathogen of an animal, preferably a pathogen of a mammal. In a preferred embodiment the micro-organism is a human pathogen.

The animal cell is preferably a tumor cell, preferably a cancer cell. The animal cell is preferably a mammalian cell, preferably a human cell. In a preferred embodiment the cancer is breast cancer, colon cancer or lung cancer.

The invention further provides a compound or a composition of the invention for use in the treatment of an animal that has or is at risk of growth of a micro-organism, an animal cell or a virus.

doses for the duration of the infection. A single dose preferably comprises between 0.5-100 mg per kg bodyweight of the compound of formula 1 and/or formula 2. In one embodiment a dose comprises 1-50 mg per kg bodyweight of the compound of formula 1 and/or formula 2. A dose may also comprise 2-25 mg per kg bodyweight of the compound of formula 1 and/or formula 2. In one aspect a dose comprises 5-10 mg per kg bodyweight of the compound of formula 1 and/or formula 2.

The invention further provides a method for the treatment of cancer comprising administering a dose of a compound of formula 1 and/or formula 2 to an individual with cancer. The compound or composition of the invention is preferably administered in one or more doses for the duration of the treatment. A single dose preferably comprises 0.5-100 mg per kg bodyweight of the compound of formula 1 and/or formula 2. In one embodiment a dose comprises 1-50 mg per kg bodyweight of the compound of formula 1 and/or formula 2. A dose may also comprise 2-25 mg per kg bodyweight of the compound of formula 1 and/or formula 2. In one aspect a dose comprises 5-10 mg per kg bodyweight of the compound of formula 1 and/or formula 2.

The invention further provides a pharmaceutical composition comprising a compound and or a composition of the invention and a pharmaceutically acceptable excipient. Further provided is a package or container designed to maintain a sterile environment comprising a pharmaceutical composition according the invention. In a preferred embodiment the package or container is aseptically provided with the pharmaceutical composition. The invention further provides a sterile package or container comprising a pharmaceutical composition of the invention.

A pharmaceutical composition comprising: a core comprising a compound of formula 1 or formula 2 and a layer of a polymeric material enveloping the core.

The compounds of the invention belong to the group of polyketides. Polyketides are a structurally very diverse family of natural products with diverse biological activities and pharmacological properties. Polyketide biosynthesis is broadly divided into three classes, mostly based on the particular type of polyketide synthases involved in their production. It was found that the biosynthesis of the compounds of the invention involves the activity of novel so-called ring-opening enzymes. The ring-opening enzymes of the invention act on polycyclic aromatic polyketides that have an anthracene or tetracene frame at one or more stages of biosynthesis. The anthracene frame is preferably a tetracyclic benz[a]anthracene.

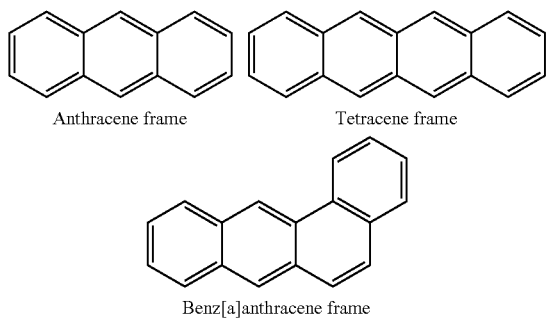

The respective frames typically have one or more substitutions at various positions. The type of substitution varies typically, but not necessarily, involves O, OH, CH3, —OCH3. Often one or more saccharides are attached to the frame. The (poly)saccharide is typically attached to the frame at one position.

In a particularly preferred embodiment the polyketide is an angucycline/angucyclinone. The terms angucyclinone and angucycine are herein defined according to the definitions in Rohr and Thiericke (1992); Angucycline group antibiotics Nat. Prod. Rep., 1992, 9, 103-137: DOI: 10.1039/NP9920900103. The terms include every natural product consisting of (or derived from) an angular tetracyclic (preferably benz[a]anthracene) structural moiety which is biosynthetically derived from a decaketide chain formed via the polyketide pathway. The term "angucycline" includes those with hydrolysable sugar (saccharide) moieties, whereas "angucyclinone" refers to a sugarless compound.

The invention further provides a *Streptomyces* bacterium, characterized by a bacterium deposited at the Centraalbureau voor Schimmelcultures (CBS) under deposit number 138593, the bacterium is preferably characterized in that the bacterium is of the strain deposited at the CBS under deposit number 138593. In a preferred embodiment the bacterium is characterized in that it produces one or more compounds of formula 1, 2, 3 and/or 4.

Further provided is a microbiological culture comprising a bacterium as defined herein above. The invention further provides a method for producing an anti-bacterial compound, the method comprising culturing a *Streptomyces* bacterium, characterized by a bacterium deposited at the CBS under deposit number 138593, the bacterium is preferably characterized in that the bacterium is of the strain deposited at the CBS under deposit number 138593. The anti-bacterial compound is preferably a compound of formula 1, 2, 3, and/or 4.

The invention further provides a method for inhibiting the growth of a bacterium, a fungus or a eukaryotic cell comprising culturing the bacterium, a fungus or a eukaryotic cell in the presence of a growth inhibiting amount of a compound of formula 1, 2, 3 and/or 4. The invention further provides a method for killing a bacterium, a fungus or a eukaryotic cell comprising culturing the bacterium, a fungus or a eukaryotic cell in the presence of a death inducing amount of a compound of formula 1, 2, 3 and/or 4. The culture is typically under conditions that would, but for the compound (s) of the invention, be permissive for growth of the bacterium, fungus or eukaryotic cell. However this is not necessarily so. It is for instance within the scope of the present invention to provide the culture with a further compound that inhibits the growth of a bacterium, a fungus or a eukaryotic cell. In such case the combination is expected to work better than either compound(s) alone.

The invention further provides a compound 5, 6, 7, 10, 11, 16, 17, 18, 19, 20, 21, 24, 26, 27, 28, 29, 30, or 31 of FIG. 1.

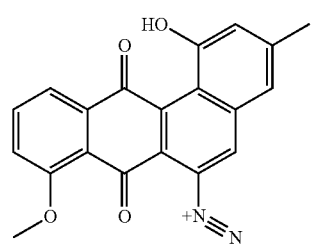

5

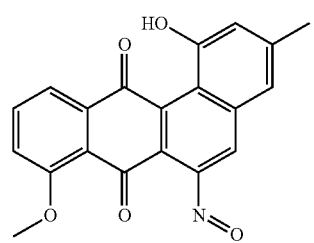

6

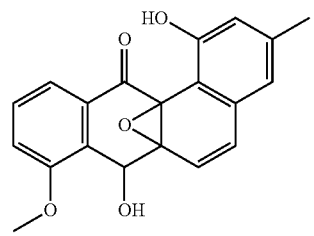

7

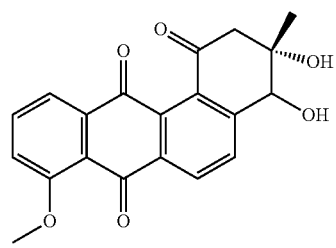

10

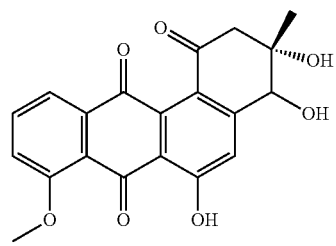

11

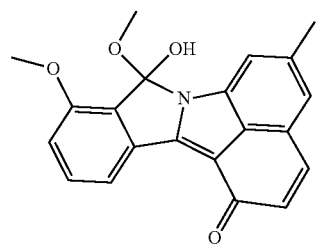 16
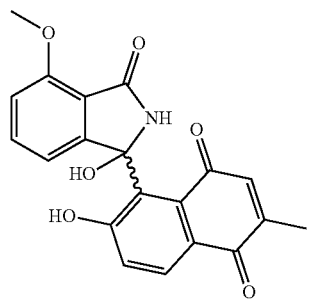 24
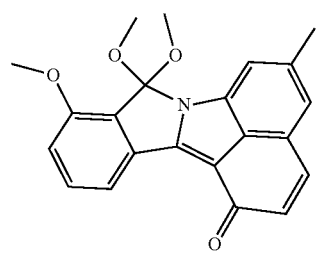 17
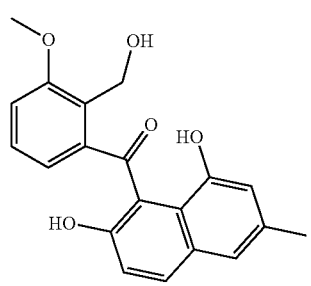 26
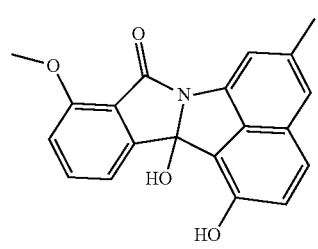 18
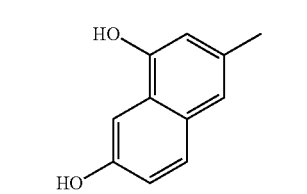 27
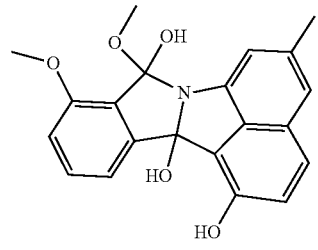 19
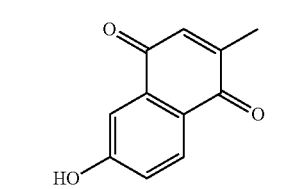 28
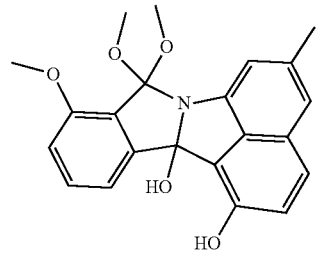 20
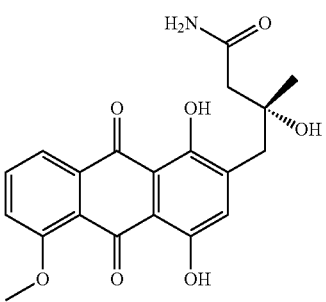 29
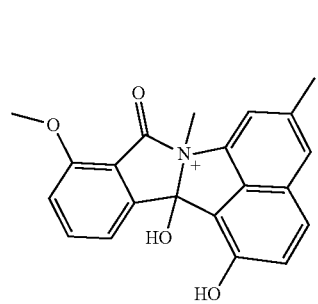 21
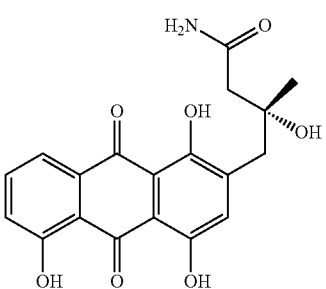 30

31

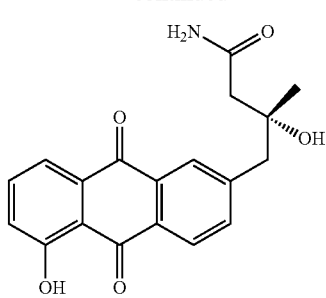

BRIEF DESCRIPTION OF THE DRAWINGS

FIG. 2. ORTEP drawing of the crystal structure of lugdunomycin (1). The dashed green line represents an intra-molecular H-bond between two hydroxyl groups (16-OH and 7-OH). The relative configurations of the five chiral centers are 9R, 16R, 17R, 19R, 21S.

FIG. 3. Biosynthetic route to lugdunomycin (1). (A) Organization of the type II PKS gene cluster (lug) responsible for lugdunomycin (1) biosynthesis in *Streptomyces* sp. QL37. Annotations of respective gene are displayed in Table 2, and genes are depicted in five different colors according to general functions. (B) Expected synthesis route for lugdunomycin and other angucyclines antibiotics presented in FIG. 1. All of the compounds in FIG. 1 are biosynthetically related. Lugdunomycin likely originates from Baeyer-Villiger oxidative cleavage at the D ring of compound 2, which is presumably executed by oxygenase lugOII. The reactive aldehyde group is thereby non-enzymatically coupled with one molecule of 3-hydroxypathalimde through Diels-Alder [4+2]cycloaddition, followed by spontaneous domino reactions, involving a sequence of Michael addition of α,β-conjugated enone with nucleophile reagent $H_2O$, nucleophilic Favorskii rearrangement, and release of one molecule of $CO_2$.

FIG. 4. HPLC-UV profiling (detected at 254 nm) confirmed lug gene cluster is responsible for angucycline biosynthesis. The angucycline/ones (such as 8 and 13) were abolished in the minimal PKS genes lugA-C null mutant.

FIG. 5. Schematic illumination of potential chemoenzymatic approach to synthesize lugdunomycin variants.

FIG. 6. Preliminary antimicrobial activity test of lugdunomycin (1) and selected angucyclines. Numbering on the paper disc corresponds to the numbering of the compounds as presented in FIG. 1, e.g. 1 stands for lugdunomycin, 6 for the novel angucycline derivative with nitroso group. Lugdunomycin (1) showed inhibition efficacy against Gram-positive bacterium *Bacillus subtilis* (A), but not against Gram-negative *Escherichia coli* JM 109 (B); All the selected angucylines simultaneously inhibited the growth of both *Bacillus subtilis* (C) and *Escherichia coli* JM109 (D). Note: compounds 8 and 9 were obtained as a mixture, which were tested activity together; AMP: positive control, ampicillin.

FIG. 7. A. Image of *Streptomyces* sp. QL37 grown on SFM agar (left) and a stereo micrograph of a single colony (right). The diameter of the agar plate was 90 mm, the diameter of the colony on the right 5 mm. B. Thin layer chromatography (TLC) analysis of the metabolome of QL37 and six randomly chosen actinomycetes from the Leiden (MBT) strain collection as comparison, all grown under six different culture conditions. Crude extracts were dissolved in ethyl acetate to a concentration of 20 mg/ml, and solutions were spotted on a TLC plate using a capillary. TLC was migrated by a solvent system of chloroform/methanol (10:1), visualized under UV at 254 nm (top), and further stained with anisaldehyde/sulfuric acid reagent by heating (bottom). Dash boxed lanes are strain QL37 grown on solid Minimal Medium (MM) agar, which gave the most spots corresponding to secondary metabolites and this suggested it was a promising strain for systematic and detailed chemical investigation.

FIG. 8. Antimicrobial activity assay of ethyl acetate extracts of the seven actinomycetes analysed by TLC in FIG. 7B, and grown under six different conditions. For each plate, from top to bottom and from left to right: (1) NMMP with mannitol (0.5% w/v) and glycerol (1% w/v); (2) NMMP pH 10; (3) Solid MM; (4) NMMP with 0.5% (w/v) Bacto yeast extract; (5) NMMP with 1% (w/v) Bacto peptone; (6) NMMP with 1% (w/v) Soy Flour. An agar diffusion assay was conducted by using *Bacillus subtilis* as indicator strain. Crude extracts were dissolved in ethyl acetate to 20 mg/mL, and 20 µL was pipetted onto a paper disc to determine the antibacterial activity. QL37 (highlighted with a dashed circle) showed better antimicrobial activity in solid MM than all modified liquid NMMP culture media and this was therefore the preferred media.

FIG. 9. Detection of Lugdunomycin (1) by thin layer chromatography (TLC). TLC was migrated by a solvent system of chloroform/methanol (10:1, $R_f$=0.26). Lugdunomycin gave a dark spot under UV at 254 nm (left), and a distinctive blue color when further stained with anisaldehyde/sulfuric acid reagent by heating (right).

FIG. 10. Racemic structure of lugdunomycin, showing the structures of lugdunomycin (+)-1 and (−)-1.

FIG. 11. 2D NMR correlations of lugdunomycin (1) and selected new angucyclines 5-7, 10, 11, 16, 18, 19, 22, 27, and 31. Displayed are HMBC ( ) and COSY (—) correlations for determination of planar structure.

FIG. 13. Budapest treaty deposit forms BP/4

EXAMPLES

Example 1

Results

Discovery of Lugdunomycin (1)

In our search for novel antibiotics, seven strains showing distinctive pigmentation were prioritized out of a unique collection of 816 actinomycetes (Zhu, H. et al 2014c), because the presence of distinctive color is a marker for secondary metabolite biosynthesis (Brady, S. F. et al, 2001). The metabolic profile of a given actinomycete is culture media-dependent, and varying growth conditions or the addition of chemical elicitors can often be applied to activate the biosynthesis of poorly expressed natural products (Zhu, H. et al 2014c). Selected actinomycetes were grown in parallel in six different culture media, and the respective metabolomes were compared by TLC analysis and antimicrobial activity assays against *Bacillus subtilis* 168. Among these, *Streptomyces* sp. QL37 grown in static MM yielded the richest metabolic profile, and was therefore subjected to large-scale (7.5 liter) fermentation. Repeated chromatographic separation of TLC-detectable compounds in the resolved crude extract (2.3 g) resulted in 1 (0.5 mg), 2 (27 mg), 8/9 (27 mg), 10 (3.4 mg), and 13 (1 mg).

Figure 12:
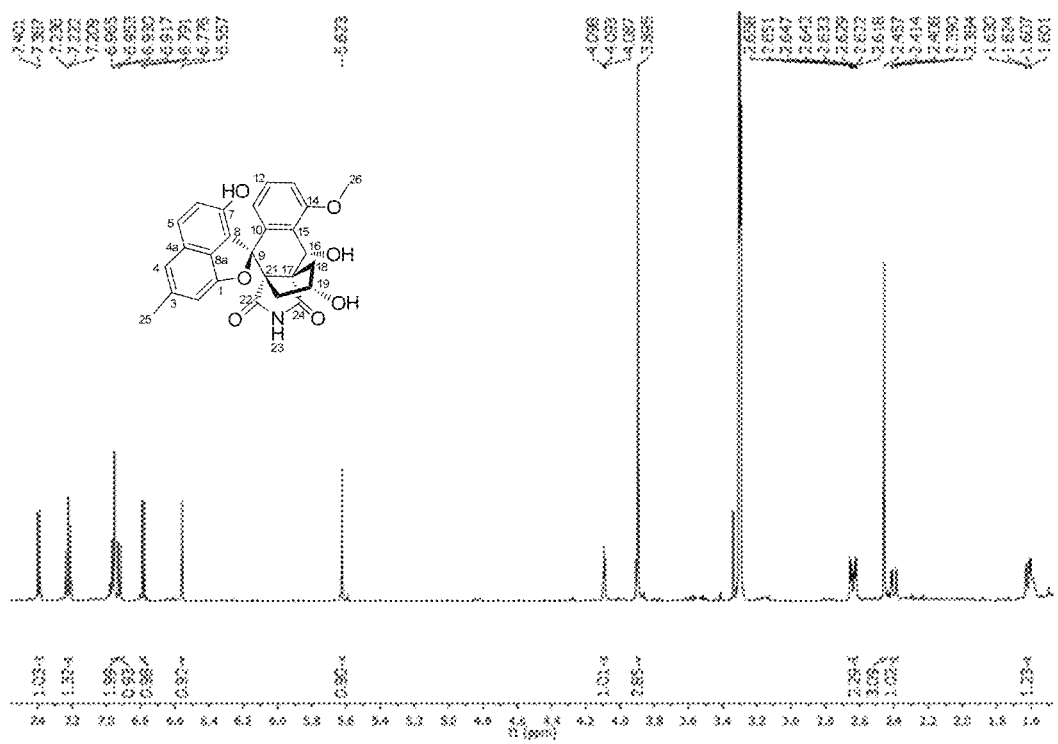
FIG. 12. Spectral list of lugdunomycin (1).
Figure 12:
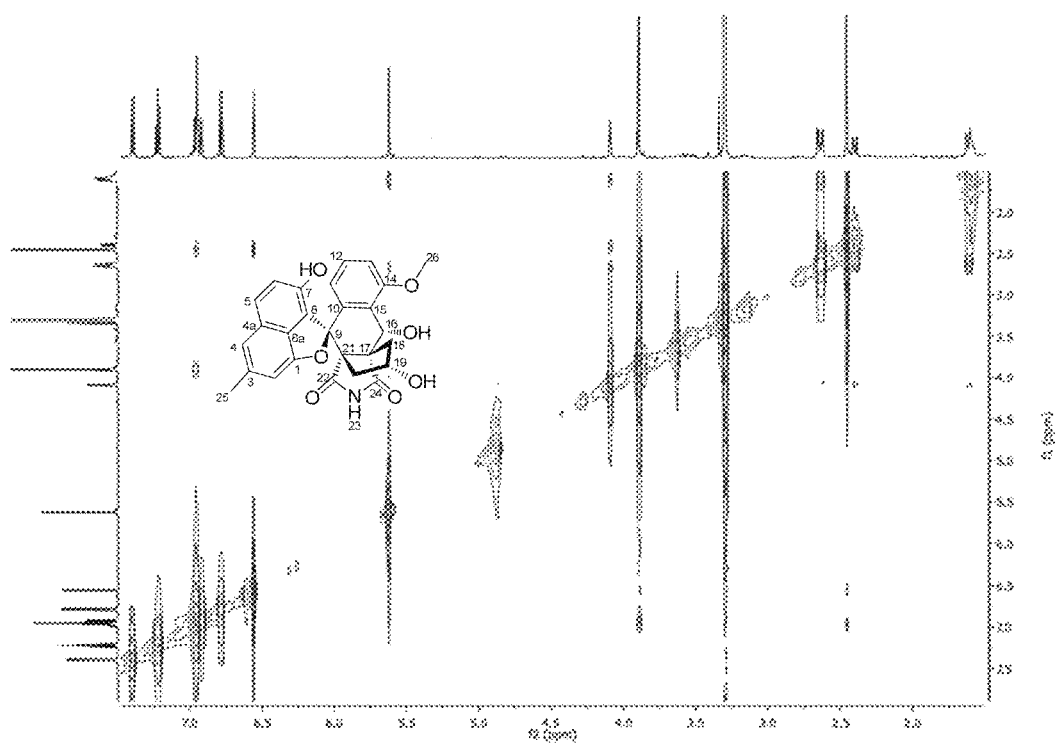
Figure 12:
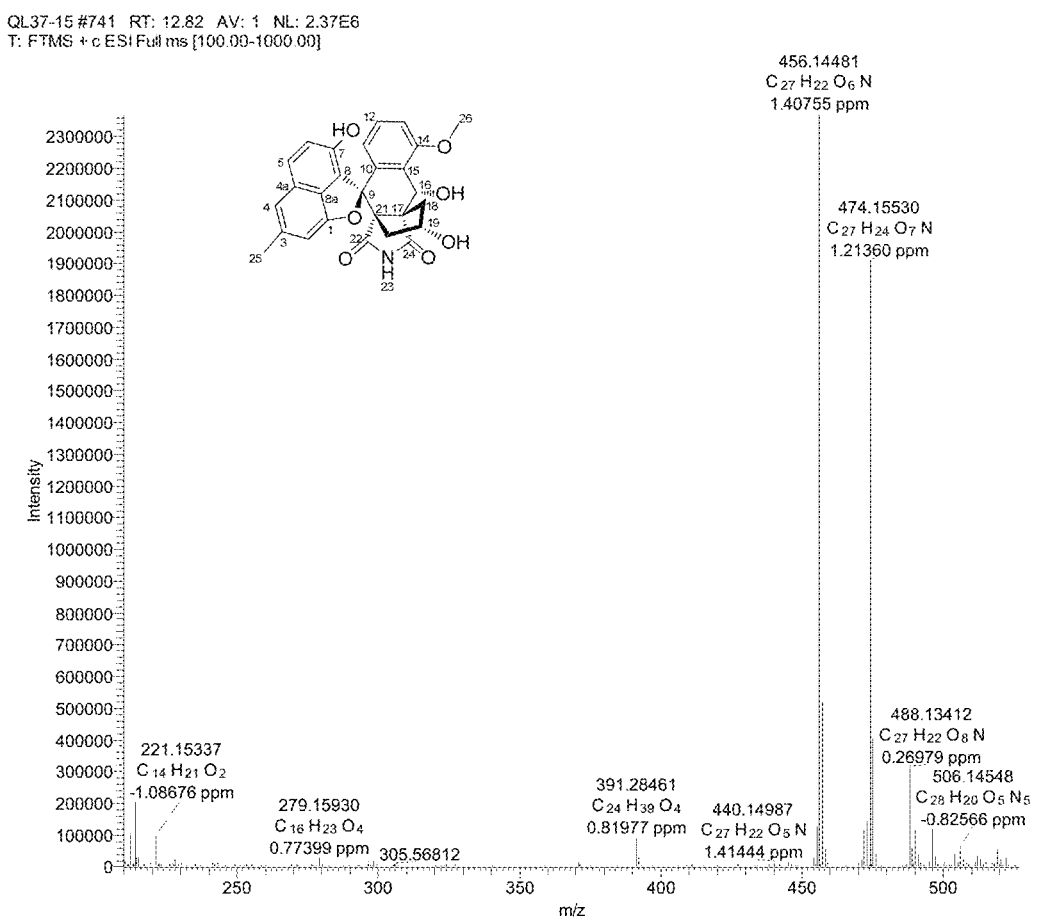
Figure 12:
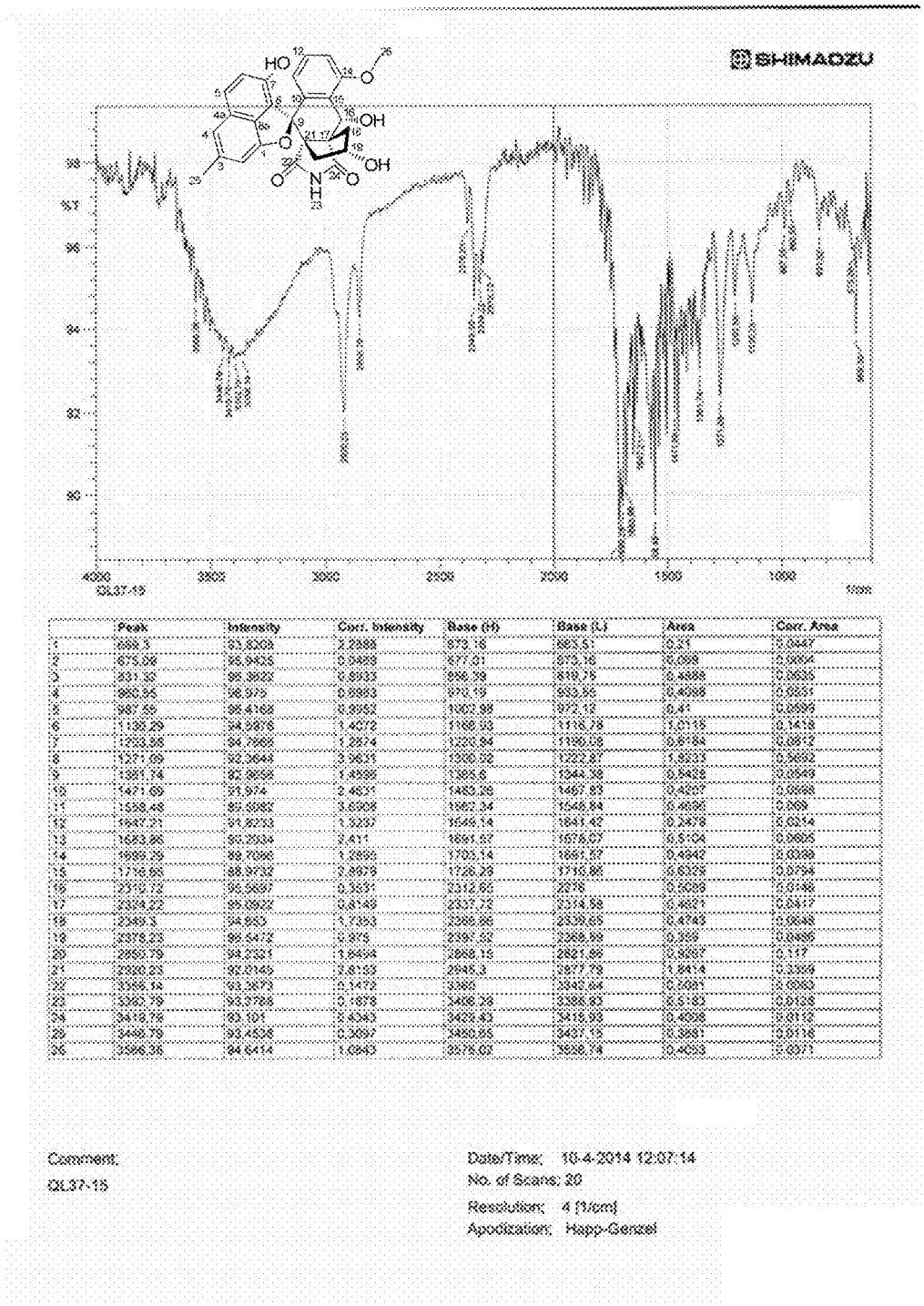

Lugdunomycin (1) was obtained as a colorless amorphous powder. UHPLC-ToF-MS analysis identified [M+H]$^+$ ion peak at m/z 474.1553 (calculated for $C_{27}H_{24}NO_7$ 474.1547) that established its molecular composition $C_{27}H_{23}NO_7$. This deduced chemical formula was corroborated by the attached proton test (APT) that exhibited 27 carbons in total. The APT experiment separated 11 carbons of CH and/or $CH_3$ downwards from 16 carbons of C and/or $CH_2$ upwards (FIG. 12). Protonated carbons were subsequently assigned by HSQC spectroscopy as two methyl groups (one methoxyl), two methylenes, nine methines (seven of which were aromatic units). Based on chemical shifts, 14 quaternary carbons were classified as two carbonyls ($\delta_C$ 182.4, and 182.5), nine olefinic carbons (three are oxygenated $\delta_C$>145, and six are non-oxygenated $\delta_C$<145), two sp$^3$ hybridization saturated atoms ($\delta_C$ 47.9, 47.3), and one unique O-bearing spiroatom at $\delta_C$ 94.8 (see below). The elucidation of three aromatic rings (ring A, B, and D) in 1 were readily assigned by the interpretation of the proton splitting pattern and COSY correlations, and further confirmed by HMBC (Table 1 and FIG. 11). $^1$H NMR spectrum exhibited typical signals attributable to a 1,2,3-trisubstituted phenyl moiety at $\delta_H$ 6.92 (brd, J=7.8 Hz, H-11), 7.22 (t, J=7.8 Hz, H-12), 6.96 (brd, J=7.8 Hz, H-13) for ring D. Ring A presented a group of coupling singlets, including two characteristic meta benzene singlets at $\delta_H$ 6.57 (brs, H-2), 6.95 (brs, H-4) secluded by an olefinic methyl at $\delta_H$ 2.46 (brs, H$_3$-25). Two distinctive aromatic doublets at $\delta_H$ 7.39 (d, J=8.4 Hz, H-5), 6.78 (d, J=8.4 Hz, H-6) were assigned to ring B. Benzene rings A and B were fused into a naphthalene system by sharing a double bond between C-4a and C-8a, which was unambiguously confirmed by several HMBC correlations, such as H-4/C-8a, H-5/C-8a, H-4/C-5, H-5/C-4, and H-6/C-4a. However, ring D was located outside the ring A/B system because no HMBC correlations were observed. Adjacent to benzene ring D, ring C was identified by the HMBC correlations from the only proton singlet at $\delta_H$ 5.62 (s, H-16) to three aromatic carbons of ring D, via $\delta_C$ 139.2 (C-10), 158.4 (C-14), and 123.1 (C-15). On the other hand, the correlations of H-16 with saturated quaternary carbons $\delta_C$ 59.8 (C-17), and 62.3 (C-21), demonstrated ring C bridging to other non-aromatic rings. Because ring C was proton-deficient (carrying only a single proton), the continued flow of structure elucidation transferred to a hydrogen-enriched fragment (—CH$_2$—CH(OH)—CH$_2$—) that was readily resolved by COSY and HMBC. Key HMBC correlations such as H-19/C-17, H-19/C-21, H-18/C-16, H-20/C-17, and H-20/C-21, etc (Table 1), unequivocally demonstrated the presence of cyclopentanol ring F, joined to ring C by sharing the bond between C-17 and C-21. Furthermore, H-18 and H-20 showed $^3J_{CH}$ HMBC correlations with two carbonyl groups at $\delta_C$ 182.4, and 182.5, respectively, which indicated the presence of another ring fused to two all-carbon quaternary stereocentres C-17 and C-21 (Minko et al., 2012) besides rings C and F; these two carbonyls had to be cyclized by a nitrogen atom in line with both the molecular formula and the chemical shifts, which was consistent with succinimide ring G. Consequently, rings D/C/F/G constituted a benzaza[4,3,3]propellane motif which is a molecule with unprecedented chemical topology [2,4-dioxo-7,8-(6-methoxyl-benzo)-3-aza[4,3,3]propellan-6,11-diol]. This ring system stereoscopically resembles a propeller the rings D/C, F, G would be the propeller's blades, and the shared C$_{17}$-C$_{21}$ bond would be its axis. The aforementioned ring systems A/B and D/C/F/G were linked at spiroatom C-9 ($\delta_C$ 94.8), which was established by the key HMBC correlations H-20/C-9, H-11/C-9, and H-6/C-9, although usual long range couplings ($^4J_{CH}$) such as H-5/C-1, and H-6/C-9 were considerably misleading (Table 1 and FIG. 11). From this we concluded that an additional five-membered furan ring (ring E) was formed to make a 2H-naphtho[1,8-bc]furan module [7-methy-2H-naphtho[1,8-bc]furan-3-ol] to join the whole structure. Due to the rigidity of naphthalene, the system of A/B/E was on the same spatial plane. Taken together, the benzaza[4,3,3]propellane skeleton is adorned with a spirocyclic 2H-naphtho[1,8-bc]furan moiety and two all-carbon quaternary centers embedded within five contiguous stereogenic carbons. The striking architecture of benzaza[4,3,3] propellane-6-spiro-2'-2H-naphtho[1,8-bc]furan has a so far unprecedented chemistry.

The planar structure was confirmed by single-crystal X-ray diffraction analysis of lugdunomycin (1) crystallized from CHCl$_3$/MeOH (10:1), and the absolute configurations of five chiral centers were accordingly determined as 9R, 16R, 17R, 19R, 21S (FIG. 2). Crystallization of 1 in a chiral space group was initially puzzling, as it exhibited a centrosymmetric space group P1 suggesting presence of a racemic mixture (FIG. 10), but enantiomers were not in a 1:1 ratio. In 3D space, an intramolecular hydrogen-bonding interaction between 16-OH (H acceptor) and 7-OH (H donor), further ensured the rigidification of backbone and fixed geometric conformation. To complicate the story more, we encountered two different crystal forms in the crystallization trial. Unfortunately, one crystal form did not diffract well enough to resolve the structure. Judging by the space group, these two crystals are diastereomers. The Diels-Alder mechanism (see FIG. 3B) echoed with the observed stereochemistry of lugdunomycin (1) in the crystallization trial. Asymmetrical 3-hydroxypathalimide employing either "endo" or "exo" transition states can lead to adducts of enantiomeric stereochemistry at four carbons, via C-9, C-17, C-19, and C-21 of lugdunomycin. Electron-withdrawing carbonyls are oriented towards the diene n system in the endo orientation, while away from it in the exo orientation. It is noteworthy that the "endo" is typically favored for rigid dienophile, which explained the unbalanced titer of enantiomers in lugdunomycin crystal. The diastereochemistry implied in crystallization experiment could arise from Michael addition step at C-16, because H$_2$O attacked the double bond from either rear or front face.

The Biosynthetic Pathway of Lugdunomycin (1)

Elucidating the biosynthesis pathway of lugdunomycin (1) is challenging, because of the high structural complexity of the molecule. It is not uncommon that a single organism simultaneously produces many structurally related analogues. The structures of the lower order intermediates or side products reflect the way the initial precursor is made, which could provide clues to elucidate the bioassembly mechanism of a higher order final product. In this sense, systematic isolation of all compounds, despite being time-consuming and labor-intensive, is not only efficient to bring to light the chemical diversity of the natural products produced by a given producer organism, but also allows dissecting unfamiliar chemical skeletons in terms of structure elucidation (2D planar connection and even 3D absolute configuration) and the biosynthetic pathway. Herein, lugdunomycin (1) was proposed to be an angucycline/one derivative, because i) compound 1 was co-isolated with angucycline/ones 2, 8-10, and 13; ii) the structural residue of rings A/B/D in 1 is exactly the same as in 2. Thereby, 2 was supposed to be the precursor of 1, but it was difficult to explain the origin of rings C, E-G, especially for the introduction of an unique nitrogen atom into the angucycline/one backbone.

Figure 1:
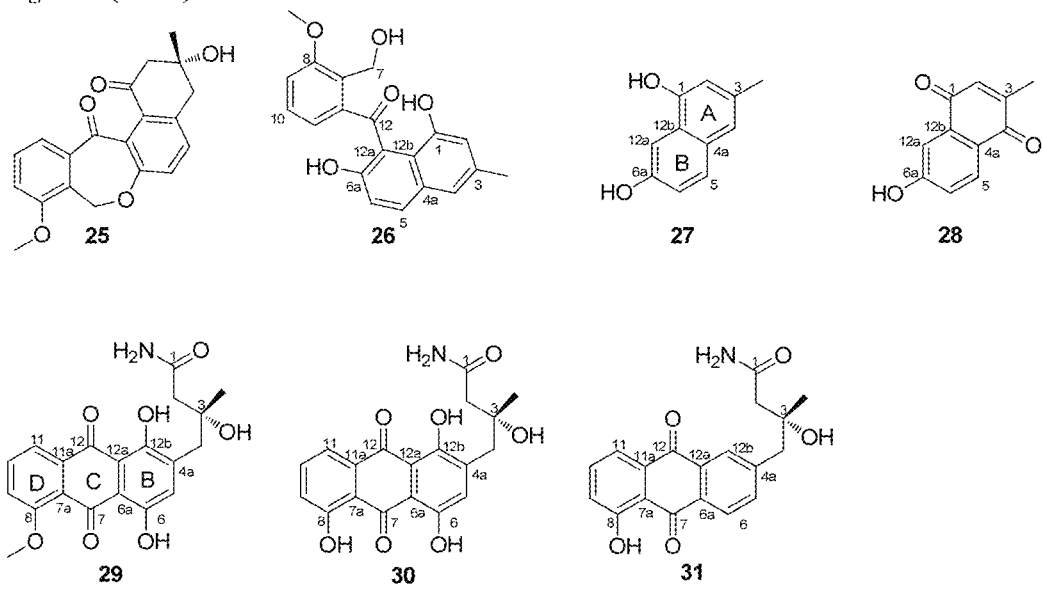
FIG. 1. Rearranged and unrearranged angucyclines from *Streptomyces* sp. QL37. Lugdunomycin (1) is a novel angucycline derivative with unprecedented skeleton. All compounds are biosynthetically related (see FIG. 3), whereby 5-7, 10, 11, 16-21, 24, 26-31 with carbon numbering, are novel compounds.

To improve the production of lugdunomycin (1) and its structurally related congeners, *Streptomyces* sp. QL37 was fermented in 77 different culture media (Table 3), varied in terms of culturing mode (liquid or solid), source of carbon, phosphate or nitrogen, pH, additional additives, etcetera. The EtOAc-resolved metabolome was analyzed by HPLC-UV (detected at 254 nm), which showed that growth on R5 agar plates with 0.8% peptone and 1% mannitol triggered the production of a considerable number of compounds with a UV spectrum analogous to lugdunomycin (1). Further UHPLC-ToF-MS analysis confirmed that these compounds indeed contained the sought-after nitrogen atom, though lugdunomycin (1) itself was not detected in the mixture. Up-scale refermentation (20 liter) of *Streptomyces* sp. QL37 followed by the extensive systematic isolation, enabled the identification of unrearranged (2-14) and rearranged (15-31) angucycline/ones (FIG. 1), whereby 5-7, 10, 11, 16-21, 24, 26-31 were previously undescribed structures. The structure identification was done on the basis of NMR (1D and/or 2D) and UHPLC-ToF-MS analysis in positive and/or negative modes, which were compared with literature spectroscopic data. The 18 compounds feature among others unique ring rearrangement/cleavage (15-31), hydration (18-21), methanolysis (16, 17, 19, 20), epoxidation (7), N-quaternary methylation (21), and amidation (15-24, and 29-31), which adds further chemical diversity and new members to the family of angucycline antibiotics. Particularly, compounds 5 and 6 possess the rare substituents diazo and nitroso group at C-6, respectively.

The co-identification of compounds 2-31 in *Streptomyces* sp. QL37 provided evidences for the biosynthetic route of lugdunomycin (1), as proposed in FIG. 3. The type II PKS-catalyzed assembly of the angucycline benz[a]anthracene backbone in itself has been well documented (Rohr et al 1992; Kharel et al 2012). A pivotal Baeyer-Villiger oxidation at the C-6a/C-7 bond of C ring initiated the structural rearrangements of precursors 2 and/or 8 into 15-31, whereas the cleavage at C-1/12b bond of A ring generated tricyclic anthraquinone scaffold 29-31. The oxidation product 2a was susceptible to hydration to afford 2b that likely serves as the key intermediate for lugdunomycin (1), as well as for all the other rearranged angucyclines 15-31. On the one hand, the —COOH group in 2b could be furnished by a putative transaminase, and a subsequent intramolecular cyclization between 7-$NH_2$ and 12-CO in the resultant amidation product 2d generated a five-membered 2-pyrrolidone ring. Another oxidative C—C cleavage at the bond C-12/12a of limamycin (Fotso, S. 2008)-like intermediate 18a (or other similar rearranged angucyclines such as 22-24) resulted in a free 3-hydroxypathalimide, which could be validated by the isolation of 27 and 28. On the other hand, the intermediate 2b could instead be transformed through intramolecular hemiacetal reaction between 1-OH and 12-CO, followed by an elimination of $H_2O$ and tautomerization to generate an unsaturated aldehyde intermediate 2c. Convergent coupling of reactive 2c and 3-hydroxypathalimide dienophile through Diels-Alder [4+2]cycloaddition constructed a complex system of benzaza[4,4,3]propellane in 1a. Lugdunomycin (1) was finally synthesized from 1a through spontaneous domino reactions, involving a sequence of Michael addition of α,β-conjugated enone with nucleophile reagent $H_2O$, nucleophilic Favorskii rearrangement, and release of one molecule of $CO_2$.

Elucidation of the biosynthesis pathway of lugdunomycin (1) by the OSMAC strategy shed light on its underlying biosynthetic machinery. Genomic mining of *Streptomyces* sp. QL37 identified a type II polyketide synthase (PKS) gene cluster (lug, Table 2 and FIG. 3A) displaying a high degree of similarity to PKS gene of urd (Faust, B. et al, 2000). Genetic inactivation of minimal PKS genes lugA-C unambiguously confirmed lug was responsible for the production of angucycline/ones in *Streptomyces* sp. QL37 (FIG. 4).

Within the lug biosynthetic gene cluster, five genes encoding putative oxygenases, namely lugOI-lugOV, attracted special attention, since multiple post-PKS oxidations were observed in the isolated angucyclines 1-31, including cleavage of C—C bonds at C-6a/C-7, C-12/12a, and C-1/12b, epoxidation at C-6a/12a, hydroxylation at C-4 and C-6. The similarity of lugOI with urdE (Decker, H. et al, 1995) suggested that this gene is most likely involved in the generation of the p-quinone motif to form the basic backbone of angucycline/one. lugOII was the best candidate for the C-6a/C-7 Baeyer-Villiger oxygenation, because it shows homologue to urdM that is reported to execute this kind of ring oxidative cleavage (Rix, U. et al, 2003). lugS encoding a putative amidotransferase domain was proposed to be responsible for the introduction of nitrogen atom, which awaits confirmation by gene disruption. Another striking feature is gene lugX, for which we failed to identify any relevant homologues in the NCBI database. Based on the predicted secondary structure of the enzyme, we anticipate that this enzyme binds thioredoxin and has reductase activity.

Efforts can be made to improve the supply of two key intermediates for Diels-Alder coupling, via 2b and 3-hydroxypathalimde. Presumably, lugOII could be exploited to increase lugdunomycin production through biochemical transformation (either in vivo or in vitro) of the abundant precursor 2. However, it is comparatively more important to overexpress the oxygenase that cleaves the bond C-12/12a, because a considerable amount of limamycins were already seen in cultures grown on R5 agar plates with peptone and mannitol, implying that the Baeyer-Villiger cleavage of C-6a/12a was not the rate-limiting step for lugdunomycin (1) synthesis. The removal of lugM encoding an O-methyltransferase probably elevate the production of lugdunomycin variant (26-O-demethylated lugdunomycin), because the methyl group blocks the proton tautomerization of 3-hydroxypathalimde into its reactive α,β-unsaturated ketone conformation, and thus hinder the key Diels-Alder reaction for the construction of benzaza[4,4,3]propellane motif in 1a (FIG. 3). Alternatively, the addition of commercial 3-hydroxypathalimde into the culture medium seems more convenient. Take together, we propose that 1) the biosynthetic route of lugdunomycin, could be used to guide in situ optimization of lugdunomycin production in *Streptomyces* sp. QL37. For instance, supplemention of Lewis acid(s) into culture medium to promote Diels-Alder reaction; 2) Lugdunomycin can be constructed through in vitro enzymatic Baeyer-Villiger oxidation to generate reactive intermediate, in tandem with semisynthetic method involving Diels-Alder coupling with 3-hydroxypathalimde; 3) By varying the dienophile reagent for Diels-Alder reaction, such as maleimide, N-hydroxyphthalimide, maleic anhydride, etc, angucycline-based lugdunomycin variants could be potentially synthesized to afford a series of variants of lugdunomycin (FIG. 5); 4) The post-PKS modification mode in lugdunomycin biosynthesis, via oxidative quinone ring opening followed by Diels-Alder coupling of extra structural unit at the reactive aldehyde site (FIG. 4), can be used to modify other PKS-type natural products, allowing the production of industrially and medicinally important chemicals based on angucyclines, but also other PKS like the linear tetracycline;

Antimicrobial Properties of Lugdunomycin (1)

The angucycline group of natural products is the largest group of polycyclic aromatic polyketides, rich in chemical scaffolds and various biological activities, predominantly anticancer and antibacterial (Kharel et al., 2012). Selected compounds displayed in FIG. 1 were tested for antimicrobial activity in an agar diffusion assay, using the Gram-positive *Bacillus subtilis* 168 and the Gram-negative *Escherichia coli* K12 as indicator strains. All tested compounds showed significant antimicrobial activity. Lugdunomycin (1) showed antimicrobial activity against *B. subtilis* (FIG. 6, A).

Materials and Methods

Microorganisms and Culturing Conditions

*Streptomyces* sp. QL37 was isolated from soil in the Qinling mountains (P. R. China) soil as described previously (Zhu et al, 2014b). The previously undescribed strain was deposited to the collection of the Centraal Bureau voor Schimmelcultures (CBS) in Utrecht, The Netherlands. *Streptomyces* sp. QL37 was cultivated on Minimal Medium agar plates (MM) (Kieser et al., 2000) with 0.5% glycerol and 1% mannitol (w/v) as the carbon sources, on R5 agar supplemented with 0.8% peptone and 1% mannitol (w/v), or to prepare spore suspensions on SFM agar plates (Soy flour man nitol; (Kieser et al., 2000)). Square agar plates (12 cm×12 cm) were inoculated with 1×10$^7$ spores from a fresh spore suspension. As indicator strains for the antibacterial assays we used *B. subtilis* 168 and *E. coli* JM109 (Sambrook et al., 1989).

General Experimental Procedures

FT-IR was measured on Perkin-Elmer FT-IR Spectrometer Paragon 1000. UV measurements were performed using a Shimadzu UV mini-1240. NMR spectra were recorded in methanol-$d_4$ on a Bruker DMX 600 MHz calibrated to a residual methanol-$d_4$ (3.30 ppm).

High resolution mass data (HRESIMS) were collected on an Agilent 1200 series HPLC connected to a LTQ-Orbitrap spectrometer. Semi-preparative HPLC (pHPLC) was performed with a Shimadzu HPLC system and a 5 mL Rheodyne manual injection loop, equipped with a reversed-phase C18 column (Phenomenex Luna C18 (2) 100 Å 5 micron 250×10 mm). All the pHPLC experiments used 2 mL/min flow rate and fraction collection based on detected peak. Silica gel (pore size 60 Å, 230-400 mesh) for open column chromatography was purchased from Sigma-Aldrich (St. Louis, Mo., USA). Pre-coated silica gel 60 F254 TLC plates (Merck, Darmstadt, Germany) were used for TLC bioautography analysis. PLC silica gel 60 F254, 1 mm (Merck, Darmstadt, Germany) was used for preparative TLC separation. Analytical TLC was performed with silica gel 60 (Merck, Darmstadt, Germany) plates using $CHCl_3$:MeOH 10:1 and visualized with anisaldehyde/sulfuric acid reagent. All solvents and chemicals were of analytical and HPLC grade.

Extraction and Isolation of Lugdunomycin (1)

The first round of systematic separation was done on MM culture medium. After seven days of growth, 225 MM agar plates inoculated with *Streptomyces* sp. QL37 were combined and cut into small blocks, which were then homogenated with a pestle. The resultant agar suspension was extracted with ethyl acetate (EtOAc) by soaking overnight at room temperature. The supernatant was filtered and subsequently evaporated under reduced pressure at 38° C. to obtain 2.3 g crude extract. This extract was adsorbed by silica gel and chromatographed on a silica gel (pore size 60 Å, 70-230 mesh, St. Louis, Mo., USA) column chromatography employing a gradient elution from n-hexane via chloroform to methanol. The combinations of fractions derived from silica gel chromatography separation were done on the basis of thin-layer chromatography (TLC) analysis (Merck, Darmstadt, Germany) using developing solvent system of chloroform and methanol (10:1). The fractions containing lugdunomycin (1) were combined by TLC detection that gave a dark spot under UV at 254 nm and a distinctive blue color when further stained with anisaldehyde/sulfuric acid reagent by heating (FIG. 9). Purification of lugdunomycin was first defatted by partition between methanol and n-hexane, and the resulting methanol phase was subsequently rechromatographed on Sephadex LH-20 column (GE Healthcare Life Sciences, Eindhoven, The Netherlands) eluting by methanol to give five subfractions. The fraction containing lugdunomycin (1) was purified by preparative TLC (Merck, Darmstadt, Germany), migrated with solvent system chloroform and methanol (9:1) and detected under UV light at 254 nm. Finally, 0.5 mg pure lugdunomycin (1) was obtained. Compounds 2 (3.4 mg), 8/9 (27 mg), 10 (3.4 mg), and 13 (1 mg) were isolated from the same MM agar plates as well.

The second round of separation was done on R5 culture media (see below). A total volume of 20 L R5 agar media was used. The subsequent fermentation and extraction methods were the same with MM culture media. UV and MS-guided separation was used to accumulate the amount of lugdunomycin (1) and isolate lugdunomycin analogues. Crude extract (20.5 g) adsorbed by silica gel was first chromatographed on a silica gel column chromatography employing gradient elution from n-hexane, chloroform, to methanol, to obtain 17 fractions. These were subsequently subjected to HPLC-UV and UHPLC-ToF-MS analysis, the combination of which was further done by UV spectrum and chemical formula. This identified among others the presence or absence of a nitrogen atom. As a result, 12 final fractions (Fr1-Fr12) were obtained. The fractions (Fr1, Fr4) abundant in already identified compounds 2, 8-10 in MM medium were discarded. Fr2 was successively chromatographed on silica gel eluting with a gradient of chloroform in n-hexane, and Sephadex LH-20 eluting with methanol, to afford pure compound 3 (2.5 mg). Fr3 was separated by silica gel eluting with a gradient of chloroform in n-hexane, to give 8 subfractions sfr3.1-sfr3.8. Sfr3.2 was separated by Sephadex LH-20, to afford the pure semi-pure purple compound 6 (0.6 mg); Sfr3.3 was purified by Sephadex LH-20, to afford the pure orange compound 15 (20 mg); Sfr3.5 was firstly separated by Sephadex LH-20 and followed by preparative TLC (PLC Silica gel 60 $F_{254}$, 1 mm, Merck, Darmstadt, Germany), migrated with solvent system of chlorofomr/methanol (10:1), to afford the semi-pure black compound 5 (0.6 mg). Fr5 was chromatographed on silica gel eluting with a gradient of methanol in chloroform, to give 5 subfractions sfr5.1-sfr5.5. Sfr5.2 was separated by Sephadex LH-20 to afford pure compound 18 (10 mg); Sfr5.4 was separated by semi-preparative reversed-phase HPLC (Phenomenex Luna C18 (2) 100 Å 5 micron 250×10 mm) on an Agilent 1200 series HPLC (Agilent technologies Inc, Santa Clara, Calif., USA), eluting with a gradient of ACN in $H_2O$ from 15% to 80% in 40 min. HPLC peaks were manually collected, resulting in the isolation of compound 10 (2.8 mg), 11 (impure, 1.0 mg), 24 (impure, 0.50 mg), 29 (semi-pure, 0.82 mg), 28 (semi-pure, 1.1 mg), 31 (semi-pure, 0.90 mg), and 30 (impure, 0.68 mg). Fr6 was directly separated by semi-preparative HPLC, eluting with a gradient of ACN in $H_2O$ from 15% to 80% in 40 min, which resulted in the separation of compound 14 (semi-pure, 0.80 mg), 7 (semi-pure, 0.40 mg), 25 (semi-pure, 0.30 mg), a mixture of 27 and 28 (semi-pure, 0.60 mg), and 26 (0.50 mg). Fr7 was directly separated by semi-preparative HPLC, eluting with a gradient of ACN in $H_2O$ from 20% to 85% in 30 min, which resulted in the isolation of 16 (semi-pure, 0.50 mg), 19 (semi-pure, 0.40 mg), and 21 (semi-pure, 0.60 mg). Fr9 was separated by silica gel eluting with a gradient of methanol in chloroform, to give 6 subfractions sfr9.1-sfr9.6. Sfr9.3 was purified by preparative TLC, migrated with solvent system of chlorofomr/methanol (5:1), to afford the pure compound 22 (5 mg) and 23 (5.5 mg).

Antimicrobial Activity Assays

Antimicrobial activity was determined using a disk diffusion assay. For this, compounds were dissolved in chloroform to a concentration of (2 μg/μL) and of this solution, 25 μL was applied on a paper disk (GE Healthcare BioSciences, Pittsburgh), except for lugdunomycin, for which 10 μL of a 1 μg/μL solution in methanol was used. The disks were then placed onto an LB agar plate overlaid with 3 ml of soft agar (LB with 0.6% (w/v) agar) containing around $5 \times 10^7$ cells of exponentially growing *Bacillus subtilis* 168 or *Escherichia coli* JM109 cells. Ampicillin was used as positive control. After incubation at 37° C. for 18 h, growth inhibition zones (in mm) were recorded as antimicrobial activity.

Example 2

Additional Data and Methods

1. Screening Promising Antibiotics Producers from In-House Actinomycete Library, and Corresponding Culture Conditions.

Our target is to find antibiotics with a novel skeleton, which are required to combat the increasingly serious multidrug-resistant pathogens such as MDR-TB (multidrug-resistant *Mycobacterium tuberculosis*), MRSA (methicillin-resistant *Staphylococcus aureus*), and multidrug-resistant Gram-negative pathogens such as *Pseudomonas aeruginosa* and *Kiebsiella pneumoniae* (Cooper and Shlaes, 2011; Rice, 2008; WHO, 2014). The presence of color in microbial cultures is often an indication of small molecules biosynthesis (Brady et al., 2001). Therefore, color can be used as an initial screen to identify microbes containing biosynthetic gene clusters for secondary metabolites production under laboratory condition. Actinomyetes showing distinctive pigmentation were screened from the collection of 816 actinomycetes (Zhu et al., 2014b) for further antibiotic screening. Our previous studies demonstrated that the culturing conditions substantially influence antibiotic production by the actinomycetes in our strain collection (Zhu et al., 2014a; Zhu et al., 2014b). Therefore, different growth conditions were considered to elicit the biosynthetic potential of selected actinomycetes from the collection. In principle, the culture media were based on minimal media supplemented with 0.5% mannitol and 1% glycerol, which were NMMP for liquid cultures and MM agar plates as solid cultures (Kieser et al., 2000). Additional additives were utilized to modify the minimal media to maximize the production of antibacterials. In total, six different culturing conditions were used to compare the secondary metabolome of the referred actinomycetes, involving NMMP, NMMP+pH 10, NMMP+soy flour (1% w/v), NMMP+yeast extract (0.5% w/v), and NMMP+peptone (1% w/v) which were previously shown to be effective growth conditions to elicit antibiotic production (Zhu et al., 2014b), as well as the standard solid MM without any additives. The incubations in parallel lasted for seven days at 30° C., and flasks containing 50 mL culture broth were shaken at 220 rpm for liquid growth condition, and square petri dishes (12 cm×12 cm) containing 50 mL MM agar were used for solid fermentation. After seven days of growth, mycelia from liquid cultures were harvested by centrifuge at 4000 rpm for 10 min. The supernatants were extracted twice with 20 mL of ethyl acetate (EtOAc). The organic phase was washed with 30 mL of water and subsequently dried with 5 g of anhydrous $Na_2SO_4$. Finally, the EtOAc was removed under vacuum at 38° C. and the residues were redissolved in 2.0 mL of EtOAc in a microtube (Eppendorf type-5415C, Harmburg, Germany). For solid MM culture, agar plates were cut into small pieces, and the agar pieces were grinded into smaller piece with pestle. The resultant agar was soaked in ethyl acetate (EtOAc) overnight in at room temperature. The EtOAc supernatant was filtered and subsequently evaporated under reduced pressure at 38° C. Residues were redissolved in 2.0 mL of EtOAc in a microtube.

Thin-layer chromatography (TLC) technique was utilized to quickly analyze the secondary metabolites produced under aforementioned six different culture conditions by seven selected actinomycetes. As exemplified in FIG. 7B, TLC (Merck, Darmstadt, Germany) analysis indicated that actinomycete QL37 (FIG. 7A) produced more metabolites when grown on solid MM as compared to other culturing conditions or to other actinomycetes.

Antimicrobial activity tests were taken into consideration, and agar diffusion assays were used for an initial screen of antimicrobial activity. Corresponding to TLC analysis (FIG. 7B), crude extracts were dissolved in ethyl acetate to a concentration of 20 mg/mL, and 20 μL of the solution was applied on a paper disk (d=6 mm). The disks were then placed onto an agar plate previously inoculated with *Bacillus subtilis*. After incubation at 37° C. for 18 h, growth inhibition zones (in mm) were recorded as antimicrobial activity. As shown in FIG. 8, antimicrobial activities of all seven actinomycetes considerably fluctuated among different culture conditions. In particular, QL37 grown solid MM showed better activity than it was in liquid NMMP, which matched the TLC result that solid culture produced more compounds than liquid cultures.

Taken together of TLC analysis and activity test result, QL37 grown MM was prioritized for new antibiotic finding in this study. Furthermore, novel antibiotics produced in trace-abundance are likely to be neglected in bioactivity-guided chromatography separation strategy, as exemplified in our previous rediscovery of known antibiotics borreldin and resistomycin (Zhu et al., 2014b), systematical phytochemical investigation strategy was instead considered to isolate as many compounds as possible, and to enlarge the possibility of finding new structures.

2. Physics Data of Lugdunomycin

Lugdunomycin (1): colorless, needle crystal, UV (MeOH) $\lambda_{max}$ (log ε) 349 (3.32), 287 (4.06), 250 (4.42) nm; ECD (MeOH) $\lambda_{max}$ (Δε) 204 (+4.49), 227 (−4.04), 251 (+0.92) nm; IR $v_{max}$ 669, 831, 1130, 1203, 1271, 1471, 1558, 1683, 1716, 2324, 2349, 2378, 2850, 2920 $cm^{-1}$; $^1H$ and $^{13}C$ NMR data, see Table 1; HRESIMS (positive mode) m/z 456.14481 $[M+H-H_2O]^+$ (calcd for $C_{27}H_{22}NO_6$ 456.14526), 474.15530 $[M+H]^+$ (calcd for $C_{27}H_2NO_7$ 474.15473).

3. Optimizing Lugdunomycin Production Conditions

*Streptomyces* sp. QL37 gave a yield of lugdunomycin in MM of 0.5 mg per 7.5 L fermentation. Varying the culturing conditions in an important method for triggering the production of bioactive compounds ((Sanchez et al., 2010; van Wezel et al., 2009; van Wezel and McDowall, 2011). Therefore, we tested different culturing conditions for the improvement of lugdunomycin production, as well as its analogues. In principle, liquid NMMP, and MM and R5 agar plates were supplemented with different carbon sources (glucose, mannitol, glycerol, xylose, GlcNAc, fructose, maltose), nitrogen sources (asparagine, $(NH_4)_2SO_4$, glutamine, arginine, proline), phosphate (TES buffer instead of usual $Na^+$—$K^+$ phosphate buffer), additional additives (soy flour, peptone, yeast extract, butyrate sodium), high salt (NaCl), and high pH (pH 10) were taken into account, according to our previous research (Zhu et al., 2014b). All the different culture media were summarized in Table 3. The incubations in parallel lasted for seven days at 30° C., and flasks containing 50 mL culture broth were shaked at 220 rpm for liquid growth condition, and square petri dishes (12 cm×12 cm) containing 50 mL agar media were used for solid fermentation. After seven-day growth, liquid cultures were harvested by centrifuge at 4000 rpm for 10 min. The supernatant were extracted twice with 20 mL of ethyl acetate (EtOAc). The organic phase was washed with 30 mL of water and subsequently dried with 5 g of anhydrous $Na_2SO_4$. Finally, the EtOAc was removed under vacuum at 38° C. and the residues were redissolved in 2.0 ml of methanol in a microtube (Eppendorf type-5415C, Harmburg, Germany). For solid culture, agar plates were cut into small pieces, and the agar pieces were grinded into smaller piece with pestle. The resultant agar was soaked in ethyl acetate (EtOAc) overnight in at room temperature. The EtOAc supernatant was filtered and subsequently evaporated under reduced pressure at 38° C. Residues were redissolved in 2.0 mL of methanol in a microtube. Thin-layer chromatography (TLC) and high performance liquid chromatography (HPLC) were used to compare lugdunomycin production under all the culture conditions listed in Table 3, by using pure lugdunomycin as reference. Preliminary TLC analysis showed *Streptomyces* sp. QL37 grown on R5-based solid agar plates gave much more complex secondary metabolites spectrum than NMMP-, and MM agar-based culture media. However, none of these culture media gave obvious blue spot of lugdunomycin when stained with anisaldehyde/sulfuric acid reagent (FIG. 9). As separation capacity of TLC was limited, HPLC-UV was considered to improve the resolution for lugdunomycin detection. HPLC analysis was performed with an Agilent 1200 series HPLC apparatus (Agilent technologies Inc, Santa Clara, Calif., USA), using a 150×4.6 mm Luna 5 micron C18 (2) 100 Å column equipped with a guard column containing C18 4×3 mm cartridges (Phenomenex Inc, Torrance, Calif., USA). The mobile phase consisted of water (A) and acetonitrile (B, HPLC grade) in a linear gradient program from 10% B to 100% B in 50 minutes at a flow rate of 1.0 mL/min. Chromatograms were recorded at 210 nm, 254 nm, and 280 nm. The injection volume was 10 µL. Corresponding to TLC analysis, HPLC analysis showed R5-based culture media gave a much more complex chromatogram than that of NMMP- and MM-based. Although lugdunomycin was still not detected, HPLC-UV showed R5-based culture media produced considerable amount of compounds giving similar UV spectrum to lugdunomycin, indicating lugdunomycin and/or its analogues. In particular, the combination of "R5+0.8% peptone+1% mannitol" gave most amounts of lugdunomycin-like compounds, and thus this culture medium was further used for another around of systematical separation for lugdunomycin accumulation purpose. To further confirm the existence of lugdunomycin analogues in "R5+0.8% peptone+1% mannitol", UHPLC-ToF-MS analysis was conducted in the crude extract and its corresponding 12 silica gel chromatography fractions.

UHPLC-ToF-MS analyses were performed on an UHPLC system (Ultimate 3000, ThermoScientific, Germany) coupled to an ESI-llQ-TOF spectrometer (micrOTOF-QII, Bruker Daltonics, Germany) in the positive mode. The chromatographic separation was done using a Kinetex $C_{18}$ UHPLC 2.6 µm particle size column 150×2.0 mm (Phenomenex, USA) at a flow rate of 0.3 mL/min and a column temperature of 30° C. Samples (3 µL) were eluted using a gradient of solvent A (water) and B (acetonitrile), both with 0.1% formic acid (v/v). The initial percentage of B was 5%, which was linearly increased to 90% in 19.5 min, followed by a 2 min isocratic period and, then re-equilibrated with original conditions in 2 min. Nitrogen was used as drying and nebulizing gas. The gas flow was set at 10.0 L/min at 250° C. and the nebulizer pressure was 2.0 bar. The MS data were acquired over m/z range of 100-1000. The capillary voltage was 3.5 kV. For internal calibration, a 10 mM solution of sodium formate (Fluka, Steinheim, Germany) was infused. Formic acid, water and acetonitrile were LCMS grade (Optima, Fisher Scientific, NJ, USA). UHPLC-ToF-MS confirmed supplemented R5 culture medium produced all the angucycline class compounds that happened in MM culture medium. More importantly, this newly found condition (R5+0.8% peptone+1% mannitol) also gave some unique chemical formula that had nitrogen atom and similar UV spectrum to lugdunomycin. Thus, UV and MS-guided separation was used in the second round of phytochemical investigation of *Streptomyces* sp. QL37.

Gene Knockout of Minimal PKS Genes lugA-C.

pSET152 was digested with PstI to obtain the oriT (RK2) fragment. This 800 bp fragment was ligated into pWHM3 digested with PstI (Garg, R. P. et al, 2010). The generated construct was used to build the disruption construct. The left flank of the gene lugA was amplified using the primers indicated in Table 4 and subsequently digested with EcoRI and XbaI. The right flank of lugC was amplified using the primers indicated in Table 4. The 1.5 kb PCR product was digested with BamHI and XbaI. Both the left flank and the right flank were first cloned into pWHM3 digested with BamHI and EcoRI. The generated construct was then digested with XbaI to include the 1.0 kb apramycin resistance cassette. The 4 kb gene disruption cassette was then digested with BamHI and EcoRI and cloned into pWHM3-oriT. The integrity of the constructs was verified by sequencing and restriction enzyme analysis. The construct was transformed to the methylase-deficient strain ET12567/pUZ8002 (Kieser et al. 2000) for conjugation to QL37. The transformants were grown to an OD value of 0.6. 100 µL of a dense QL37 spore prep (10^8 spores/ml) in 500 µl 2×YT was incubated for 10 min at 50° C. to induce germination. The spores were cooled down under tap water and the spores were further incubated at 30° C. for three hours. The germinated spore suspension was mixed with 600 µL of ET12567/pUZ8002 (Kieser, T. et al, 2000) carrying the disruption construct. This mix was centrifuged and supernatant was discarded. The pellet was resuspended in 100 µL and plated out on SFM containing 60 mM $MgCl_2$ and 60 mM $CaCl_2$ (Wang and Jin 2014). After overnight incubation at 30° C. the plate was overlayed with 50 µg/mL apramycin and 10 µg/mL nalidixic acid. After seven days incubation the colonies were transferred to a new SFM plate supplemented with 50 µg/mL apramycin and to and to a SFM plate containing 20 µg/mL thiostrepton. The colonies resistant to apramycin and sensitive to thiostrepton were selected and grown on SFM for preparation of a spore suspension. To confirm the loss of thiostrepton-resistance, dilution series were prepared and grown on SFM plate containing 20 μg/mL thiostrepton. All the used primers are summarized in Table 4.

CITED ART

Brady, S. F., Chao, C. J., Handelsman, J., and Clardy, J. (2001) Cloning and heterologous expression of a natural product biosynthetic gene cluster from eDNA. *Org Lett* 3: 1981-1984.

Cooper, M. A., and Shlaes, D. (2011) Fix the antibiotics pipeline. *Nature* 472: 32.

Decker, H.; Haag, S. Cloning and characterization of a polyketide synthase gene from *Streptomyces fradiae* Tu2717, which carries the genes for biosynthesis of the angucycine antibiotic urdamycin A and a gene probably involved in its oxygenation. J. Bacteriol. 1995, 177, 6126-6136.

Faust, B.; Hoffmeister, D.; Weitnauer, G.; Westrich, L.; Haag, S.; Schneider, P.; Decker, H.; Künzel, E.; Rohr, J.; Bechthold, A. Two new tailoring enzymes, a glycosyltransferase and an oxygenase, involved in biosynthesis of the angucycine antibiotic urdamycin A in *Streptomyces fradiae* Tu2717. Microbiology 2000, 146, 147-154.

Fotso, S.; Mahmud, T.; Zabriskie, T. M.; Santosa, D. A.; Proteau, P. J. Rearranged and Unrearranged Angucyclinones from Indonesian *Streptomyces* spp. J. Antibiot. (Tokyo). 2008, 61, 449-456.

Garg, R. P.; Parry, R. J. Regulation of valanimycin biosynthesis in *Streptomyces viridifaciens*: Characterization of VlmI as a *Streptomyces* antibiotic regulatory protein (SARP). Microbiology 2010, 156, 472-483

Kharel, M. K., Pahari, P., Shepherd, M. D., Tibrewal, N., Nybo, S. E., Shaaban, K. A., and Rohr, J. (2012) Angucyclines: Biosynthesis, mode-of-action, new natural products, and synthesis. *Nat Prod Rep* 29: 264-325.

Kieser, T., Bibb, M. J., Buttner, M. J., Chater, K. F., and Hopwood, D. A. (2000) *Practical Streptomyces genetics*. Norwich, U.K.: John Innes Foundation.

Kwon, S. J., Lee, M. Y., Ku, B., Sherman, D. H., and Dordick, J. S. (2007) High-throughput, microarray-based synthesis of natural product analogues via in vitro metabolic pathway construction. *ACS Chem Biol* 2: 419-425.

Minko, Y., Pasco, M., Lercher, L., Botoshansky, M., and Marek, I. (2012) Forming all-carbon quaternary stereogenic centres in acyclic systems from alkynes. *Nature* 490: 522-526.

Rice, L. B. (2008) Federal funding for the study of antimicrobial resistance in nosocomial pathogens: no ESKAPE. *J Infect Dis* 197: 1079-1081.

Rix, U.; Remsing, L. L.; Hoffmeister, D.; Bechthold, A.; Rohr, J. Urdamycin L: A novel metabolic shunt product that provides evidence for the role of the urdM gene in the urdamycin A biosynthetic pathway of *Streptomyces fradiae* TÜ 2717. ChemBioChem 2003, 4, 109-111.

Rohr, J., and Thiericke, R. (1992) Angucycline group antibiotics. *Nat Prod Rep* 9: 103-137.

Sambrook, J., Fritsch, E. F., and Maniatis, T. (1989) *Molecular cloning: a laboratory manual*. Cold Spring harbor, N.Y.: Cold Spring Harbor laboratory press.

Sanchez, S., Chavez, A., Forero, A., Garcia-Huante, Y., Romero, A., Sanchez, M., Rocha, D., Sanchez, B., Avalos, M., Guzman-Trampe, S., Rodriguez-Sanoja, R., Langley, E., and Ruiz, B. (2010) Carbon source regulation of antibiotic production. *J Antibiot* (Tokyo) 63: 442-459.

Shen, B. (2003) Polyketide biosynthesis beyond the type I, II and III polyketide synthase paradigms. *Curr Opin Chem Biol* 7: 285-295.

Staunton, J., and Weissman, K. J. (2001) Polyketide biosynthesis: a millennium review. *Nat Prod Rep* 18: 380-416.

Tibrewal, N., Pahari, P., Wang, G., Kharel, M. K., Morris, C., Downey, T., Hou, Y., Bugni, T. S., and Rohr, J. (2012) Baeyer-Villiger C—C bond cleavage reaction in gilvocarcin and jadomycin biosynthesis. *J Am Chem Soc* 134: 18181-18184.

van Wezel, G. P., McKenzie, N. L., and Nodwell, J. R. (2009) Chapter 5. Applying the genetics of secondary metabolism in model actinomycetes to the discovery of new antibiotics. *Methods Enzymol* 458: 117-141.

van Wezel, G. P., and McDowall, K. J. (2011) The regulation of the secondary metabolism of *Streptomyces*: new links and experimental advances. *Nat Prod Rep* 28: 1311-1333.

WHO (2014) *Antimicrobial Resistance. Global Report on Surveillance*. Geneva, Switzerland.

Zhu, H., Sandiford, S. K., and van Wezel, G. P. (2014a) Triggers and cues that activate antibiotic production by actinomycetes. *J Ind Microbiol Biotechnol* 41: 371-386.

Zhu, H., Swierstra, J., Wu, C., Girard, G., Choi, Y. H., van Wamel, W., Sandiford, S. K., and van Wezel, G. P. (2014b) Eliciting antibiotics active against the ESKAPE pathogens in a collection of actinomycetes isolated from mountain soils. *Microbiology* 160: 1714-1725.

Zhu, H.; Swierstra, J.; Wu, C.; Girard, G.; Choi, Y. H.; van Wamel, W.; Sandiford, S. K.; van Wezel, G. P. Eliciting antibiotics active against the ESKAPE pathogens in a collection of actinomycetes isolated from mountain soils. Microbiology 2014c, 160, 1714-1725.

TABLE 1

$^1$H and $^{13}$C NMR data for Lugdunomycin (1) [a]

| NO. | $\delta_C$ | $\delta_H$ (J in Hz) | HMBC [b] | COSY | NOESY |
|---|---|---|---|---|---|
| 1 | 158.8 | | | | |
| 2 | 102.4 | 6.57 (brs) | C-8a, C-4, C-25 | H-4, H-25 | H-25 |
| 3 | 136.2 | | | | |
| 4 | 115.7 | 6.95 (brs) | C-8a, C-2, C-25, C-5 | H-2, H-25 | H-25 |
| 4a | 127.4 | | | | |
| 5 | 127.1 | 7.39 (d, J = 8.4 Hz, 1H) | C-4, C-8a, C-7, C-6, C-1*, C-8* | H-6 | |
| 6 | 123.9 | 6.78 (d, J = 8.4 Hz, 1H) | C-4a, C-8, C-7, C-9* | H-5 | |
| 7 | 148.2 | | | | |
| 8 | 122.3 | | | | |
| 8a | 129.1 | | | | |
| 9 | 94.8 | | | | |
| 10 | 139.2 | | | | |
| 11 | 119.7 | 6.92 (brd, J = 7.8 Hz, 1H) | C-9, C-13, C-15 | H-12, H-13 | |

TABLE 1-continued $^1$H and $^{13}$C NMR data for Lugdunomycin (1) $^a$

| NO. | $\delta_C$ | $\delta_H$ (J in Hz) | HMBC $^b$ | COSY | NOESY |
|---|---|---|---|---|---|
| 12 | 130.9 | 7.22 (t, J = 7.8 Hz, 1H) | C-10, C-14, C-13, C-11 | H-11, H-13 | |
| 13 | 111.1 | 6.96 (brd, J = 7.8 Hz, 1H) | C-11, C-15, C-14 | H-12, H-11 | H-26 |
| 14 | 158.4 | | | | |
| 15 | 123.1 | | | | |
| 16 | 62.6 | 5.62 (s) | C-15, C-14, C-10, C-17, C-18, C-21 | | H-18b, H-20a |
| 17 | 59.8 | | | | |
| 18 | 47.9 | 2.64 (m, H-18a); | C-24, C-19, C-20, C-16 | H-18b | H-18b, H-20b |
|    |      | 1.62 (dd, J = 13.8, 3.6 Hz, H-18b) | C-24, C-17, C-16, C-19 | H-19, H-18a | H-20a, H-16, H-19, H-18a |
| 19 | 70.5 | 4.09 (t, J = 3.6 Hz, 1H) | C-17, C-18, C-20, C-21 | H-18b, H-20b | H-18b, H-20b, H-20a |
| 20 | 47.3 | 2.63 (m, H-20a) | C-17, C-19, C-18, C-22 | H-20b | H-19, H-18b |
|    |      | 2.40 (dd, J = 14.4, 3.6 Hz, H-20b) | C-22, C-9, C-21 | H-19, H-20a | H-19, H-18a, H-20a |
| 21 | 62.3 | | | | |
| 22 | 182.5 | | | | |
| 23 | —NH | | | | |
| 24 | 182.4 | | | | |
| 25 | 22.1 | 2.46 (brs, 3H) | C-2, C-3, C-4 | H-2, H-4 | H-2, H-4 |
| 26 | 56.1 | 3.90 (s, 3H) | C-14 | | H-13 |

$^a$ 1 recorded in CD$_3$OD. Proton coupling constants (J) in Hz are given in parentheses. $^1$H NMR and $^{13}$C APT NMR spectra were recorded at 600 MHz. All chemical shift assignments were done on the basis of 1D and 2D NMR techniques.
$^b$ All observed HMBC, COSY, and NOESY correlations are summarized, and long range coupling ($^4J_{CH}$) in HMBC was marked with asterisk (*).

TABLE 2

Gene organization of the angucycline biosynthetic gene cluster (lug) of *Streptomyces* sp. QL37.

| ORF | Protein | Distribution | AA | Putative function | Nearest homologue | Homology | Accession |
|---|---|---|---|---|---|---|---|
| 1 | LugRI | Prokka_02560 | 379 | XRE-family regulator | *Streptomyces griseoaurantiacus* M045 | 80% | EGG46652.1 |
| 2 | LugU | Prokka_02561 | 284 | ADP-ribose pyrophosphatase | *Streptomyces aurantiacus* JA 4570 | 84% | EPH39897.1 |
| 3 | LugV | Prokka_02562 | 144 | hypothetical protein | *Streptomyces aureofaciens* | 76% | WP_052839114.1 |
| 4 | LugW | Prokka_02563 | 199 | NADPH-dependent FMN reductase | *Streptomyces* sp. 303MFCol5.2 | 85% | WP_020127613.1 |
| 5 | LugRII | Prokka_02564 | 280 | XRE family transcriptional regulator | *Streptomyces sviceus* | 81% | WP_007383482.1 |
| 6 | LugRIII | Prokka_02565 | 223 | LuxR family transcriptional regulator | *Streptomyces* sp. W007 | 52% | WP_007453015.1 |
| 7 | LugRIV | Prokka_02566 | 239 | TetR family transcriptional regulator | *Streptomyces* sp. W007 | 67% | WP_007453018.1 |
| 8 | LugTI | Prokka_02567 | 493 | putative export protein | *Streptomyces* sp. W007 | 76% | WP_007453020.1 |
| 9 | LugX | Prokka_02568 | 144 | hypothetical protein | — | — | — |
| 10 | LugM | Prokka_02569 | 346 | O-methyltransferase (tcmO) | *Streptomyces* sp. W007 | 71% | WP_007453021.1 |
| 11 | LugOI | Prokka_02570 | 490 | Monooxygenase (urdE) | *Streptomyces* sp. W007 | 81% | WP_007453024.1 |
| 12 | LugF | Prokka_02571 | 109 | polyketide cyclase (urdF) | *Streptomyces* sp. SCC 2136 | 80% | CAH10118.1 |
| 13 | LugA | Prokka_02572 | 427 | polyketide α-ketoacyl synthase II (urdA) | *Streptomyces* sp. W007 | 87% | WP_007453026.1 |
| 14 | LugB | Prokka_02573 | 407 | polyketide β-ketoacyl synthase (urdB) | *Streptomyces* sp. W007 | 80% | WP_007453027.1 |
| 15 | LugC | Prokka_02574 | 91 | Acyl carrier protein (urdC) | *Streptomyces* sp. W007 | 71% | WP_007453028.1 |
| 16 | LugD | Prokka_02575 | 262 | ketoacyl reductase (urdD) | *Streptomyces* sp. W007 | 83% | WP_007453030.1 |
| 17 | LugE | Prokka_02576 | 316 | aromatase | *Streptomyces* sp. W007 | 79% | WP_007453031.1 |
| 18 | LugOII | Prokka_02577 | 656 | monooxygenase (urdM) | *Streptomyces* sp. W007 | 76% | WP_007453032.1 |
| 19 | LugG | Prokka_02578 | 262 | NAD(P)H dependent dehydrogenase | *Streptomyces* sp. W007 | 76% | WP_007453033.1 |
| 20 | LugH | Prokka_02579 | 527 | methylmalonyl-CoA carboxyltransferase | *Streptomyces* sp. W007 | 87% | WP_007453034.1 |
| 21 | LugI | Prokka_02580 | 79 | putative acetyl-CoA carboxylase | *Streptomyces rapamycinicus* | 61% | WP_020868207.1 |
| 22 | LugJ | Prokka_02581 | 417 | putative MFS-type transporter EfpA | *Streptomyces* sp. 303MFCol5.2 | 62% | WP_020130977.1 |
| 23 | LugK | Prokka_02582 | 195 | NAD(P)H-dependent FMN reductase | *Streptomyces fradiae* | 66% | KDS84998.1 |
| 24 | LugOIII | Prokka_02583 | 214 | putative monooxygenase | *Streptomyces* sp. W007 | 62% | WP_007450404.1 |
| 25 | LugL | Prokka_02584 | 245 | phosphopantetheinyl transferase | *Streptomyces venezuelae* | 51% | WP_015037371.1 |
| 26 | LugRV | Prokka_02585 | 267 | transcriptional regulatory protein BaeR | *Streptomyces* sp. W007 | 66% | WP_007450396.1 |
| 27 | LugTII | Prokka_02586 | 458 | MFS transporter | *Streptomyces ochraceisclerroticus* | 76% | WP_051862838.1 |
| 28 | LugN | Prokka_02587 | 307 | thioesterase | *Streptomyces scopuliridis* | 69% | WP_030349255.1 |
| 29 | LugOIV | Prokka_02588 | 275 | oxidoreductase | *Streptomyces* sp. W007 | 70% | WP_050987713.1 |
| 30 | LugRVI | Prokka_02589 | 646 | SARP family transcriptional regulator | *Streptomyces* sp. W007 | 57% | WP_007450402.1 |
| 31 | LugOV | Prokka_02590 | 229 | putative dehydrogenase-methyltransferase | *Streptomyces* sp. W007 | 57% | WP_007450403.1 |
| 32 | LugP | Prokka_02591 | 425 | phosphoribosyltransferase | *Streptomyces pratensis* | 90% | WP_014156222.1 |
| 33 | LugTIII | Prokka_02592 | 1032 | secreted protein | *Streptomyces pristinaespiralis* ATCC 25486 | 81% | EDY62729.1 |
| 34 | LugQ | Prokka_02593 | 869 | hypothetical protein | *Streptomyces pristinaespiralis* | 73% | WP_053557574.1 |
| 35 | LugS | Prokka_02594 | 1134 | putative Type 1 glutamine amidotransferase | *Streptomyces pristinaespiralis* | 75% | WP_005320663.1 |

TABLE 2-continued

Gene organization of the angucycline biosynthetic gene cluster (lug) of *Streptomyces* sp. QL37.

| ORF | Protein | Distribution | AA | Putative function | Nearest homologue | Homology | Accession |
|---|---|---|---|---|---|---|---|
| 36 | LugY | Prokka_02595 | 1093 | hypothetical protein | *Streptomyces pristinaespiralis* | 78% | WP_005320665.1 |
| 37 | LugZ | Prokka_02596 | 185 | acetyltransferase | *Streptomyces* sp. W007 | 72% | WP_032790623.1 |

TABLE 3

Culture media with different components combination for lugdunomycin production.

No. Media Combination

1. NMMP + 0.2% L-asparagine + 50 mM TES buffer + 2% glycerol
2. NMMP + 0.2% L-asparagine + 50 mM TES buffer + 1% glucose
3. NMMP + 0.2% L-asparagine + 50 mM TES buffer + 1% mannitol
4. NMMP + 0.2% L-asparagine + 50 mM TES buffer + 1% xylose
5. NMMP + 0.2% L-asparagine + 50 mM TES buffer + 1% GluNAc
6. NMMP + 0.2% $(NH_4)_2SO_4$ + 50 mM TES buffer + 1% glycerol
7. NMMP + 0.2% $(NH_4)_2SO_4$ + 50 mM TES buffer + 1% glucose
8. NMMP + 0.2% $(NH_4)_2SO_4$ + 50 mM TES buffer + 1% mannitol
9. NMMP + 0.2% $(NH_4)_2SO_4$ + 50 mM TES buffer + 1% xylose
10. NMMP + 0.2% $(NH_4)_2SO_4$ + 50 mM TES buffer + 1% GluNAc
11. NMMP + 0.2% L-glutamine + 50 mM TES buffer + 1% glycerol
12. NMMP + 0.2% L-glutamine + 50 mM TES buffer + 1% glucose
13. NMMP + 0.2% L-glutamine + 50 mM TES buffer + 1% mannitol
14. NMMP + 0.2% L-glutamine + 50 mM TES buffer + 1% xylose
15. NMMP + 0.2% L-glutamine + 50 mM TES buffer + 1% GluNAc
16. NMMP + 0.2% L-glutamine + 50 mM TES buffer + 1% fructose
17. NMMP + 0.2% L-glutamine + 50 mM TES buffer + 1% maltose
18. NMMP + 0.2% L-arginine + 50 mM TES buffer + 1% glycerol
19. NMMP + 0.2% L-arginine + 50 mM TES buffer + 1% glucose
20. NMMP + 0.2% L-arginine + 50 mM TES buffer + 1% mannitol
21. NMMP + 0.2% L-arginine + 50 mM TES buffer + 1% xylose
22. NMMP + 0.2% L-arginine + 50 mM TES buffer + 1% GluNAc
23. NMMP + 0.2% L-arginine + 50 mM TES buffer + 1% fructose
24. NMMP + 0.2% L-arginine + 50 mM TES buffer + 1% maltose
25. NMMP + 0.2% L-proline + 50 mM TES buffer + 1% glycerol
26. NMMP + 0.2% L-proline + 50 mM TES buffer + 1% glucose
27. NMMP + 0.2% L-proline + 50 mM TES buffer + 1% mannitol
28. NMMP + 0.2% L-proline + 50 mM TES buffer + 1% xylose
29. NMMP + 0.2% L-proline + 50 mM TES buffer + 1% GluNAc
30. NMMP + 0.2% L-proline + 50 mM TES buffer + 1% fructose
31. NMMP + 0.2% L-proline + 50 mM TES buffer + 1% maltose
32. NMMP + 0.2% $(NH_4)_2SO_4$ + phosphate buffer + 1% glycerol + 0.5% mannitol
33. NMMP + 0.2% $(NH_4)_2SO_4$ + phosphate buffer + 1% glycerol + 0.5% mannitol + 1% SFM
34. NMMP + 0.2% $(NH_4)_2SO_4$ + phosphate buffer + 1% glycerol + 0.5% mannitol + 0.5% yeast extract
35. NMMP + 0.2% $(NH_4)_2SO_4$ + phosphate buffer + 1% glycerol + 0.5% mannitol + 1% peptone
36. NMMP + 0.2% $(NH_4)_2SO_4$ + phosphate buffer + 1% glycerol + 0.5% mannitol + pH 10
37. MM + 0.5% yeast extract + 1% mannitol
38. MM + 0.5% yeast extract + 1% glucose
39. MM + 0.5% yeast extract + 1% glycerol
40. MM + 0.5% yeast extract + 50 mM GluNAc
41. MM + 0.8% peptone + 1% mannitol
42. MM + 0.8% peptone + 1% glucose
43. MM + 0.8% peptone + 1% glycerol
44. MM + 0.8% peptone + 50 mM GluNAc
45. MM + 1% mannitol
46. MM + 1% glucose
47. MM + 1% glycerol
48. MM + 50 mM GluNAc
49. MM + 25 mM NaBu + 1% mannitol
50. MM + 25 mM NaBu + 1% glucose
51. MM + 25 mM NaBu + 1% glycerol
52. MM + 25 mM NaBu + 50 mM GluNAc
53. R5 + proline + NaOH + CaCl2 + 1% glucose
54. R5 + proline + NaOH + CaCl2 + 1% glycerol
55. R5 + proline + NaOH + CaCl2 + 1% mannitol
56. R5 + proline + NaOH + CaCl2 + 1% 50 mM GluNAc
57. R5 + proline + NaOH + CaCl2 + without sugar
58. R5 + 1% glucose
59. R5 + 1% glycerol
60. R5 + 1% mannitol
61. R5 + 50 mM GluNAc
62. R5 + without sugar TABLE 3-continued Culture media with different components combination for lugdunomycin production.

No. Media Combination

63  R5 + 200 mM NaCl + 1% glucose
64  R5 + 200 mM NaCl + 1% glycerol
65  R5 + 200 mM NaCl + 1% mannitol
66  R5 + 200 mM NaCl + 50 mM GluNAc
67  R5 + 200 mM NaCl + without sugar
68  R5 + 0.8% peptone + 1% glucose
69  R5 + 0.8% peptone + 1% glycerol
70  R5 + 0.8% peptone + 1% mannitol
71  R5 + 0.8% peptone + 50 mM GluNAc
72  R5 + 0.8% peptone + without sugar
73  R5 + 0.5% Yeast extract + 1% glucose
74  R5 + 0.5% Yeast extract + 1% glycerol
75  R5 + 0.5% Yeast extract + 1% mannitol
76  R5 + 0.5% Yeast extract + 50 mM GluNAc
77  R5 + 0.5% Yeast extract + without sugar

TABLE 4

Primers used for gene knockout of minimal PKS genes lugA-lugC.

| | |
|---|---|
| MinPKS_LF_Fw | CGATGAATTCCCGCCACCACCGAGCTCTTC |
| MinPKS_LF_RV | GAAGTTATCCATCACCTCTAGAGATACCGGTGATGACGACCC |
| MinPKS_RF_Fw | GAAGTTATCGCGCATCTCTAGAGCCGAGCAGCTCGACCGTTAC |
| MinPKS_RF_Rv | CGATGGATCCCTGCCCTTGTCGAGAAGCAGTG |

SEQUENCE LISTING

<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: primer

<400> SEQUENCE: 1
cgatgaattc cgccaccac cgagctcttc                                    30

<210> SEQ ID NO 2
<211> LENGTH: 42
<212> TYPE: DNA
<213> ORGANISM: Artificial Sequence
<220> FEATURE:
<223> OTHER INFORMATION: primer

<400> SEQUENCE: 2
gaagttatcc atcacctcta gagataccgg tgatgacgac cc                      42

<210> SEQ ID NO 3
<211> LENGTH: 43
<212> TYPE: DNA
<213> ORGANISM: Artificial Sequence
<220> FEATURE:
<223> OTHER INFORMATION: primer

<400> SEQUENCE: 3
gaagttatcg cgcatctcta gagccgagca gctcgaccgt tac                     43

<210> SEQ ID NO 4
<211> LENGTH: 32
<212> TYPE: DNA

```
<213> ORGANISM: Artificial Sequence
<220> FEATURE:
<223> OTHER INFORMATION: primer

<400> SEQUENCE: 4
cgatggatcc ctgcccttgt cgagaagcag tg                                32
```

33
-continued
7
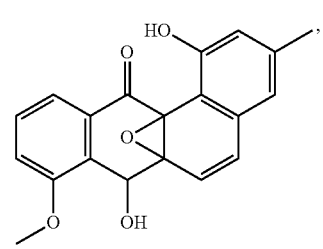
10
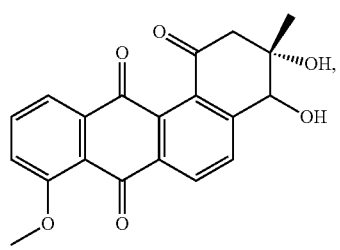
11
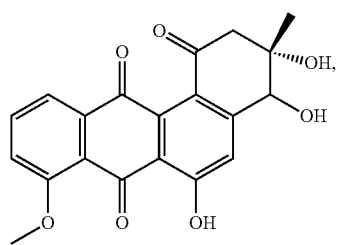
16
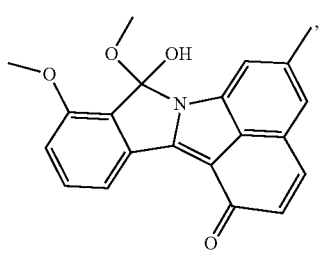
18
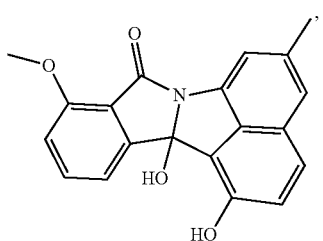
19
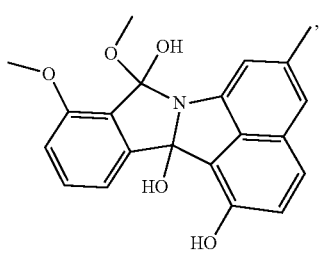
34
-continued
20
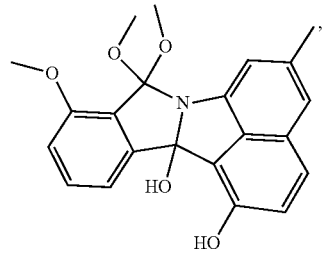
21
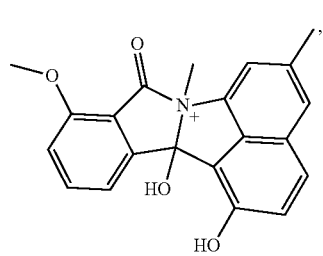
24
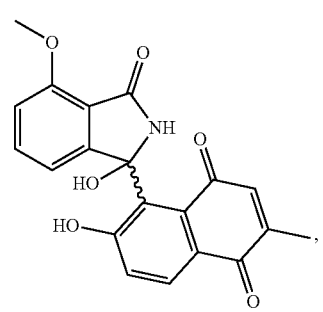
26
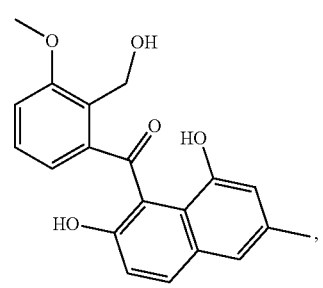
27
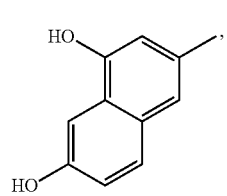
29
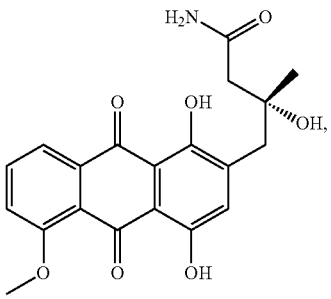

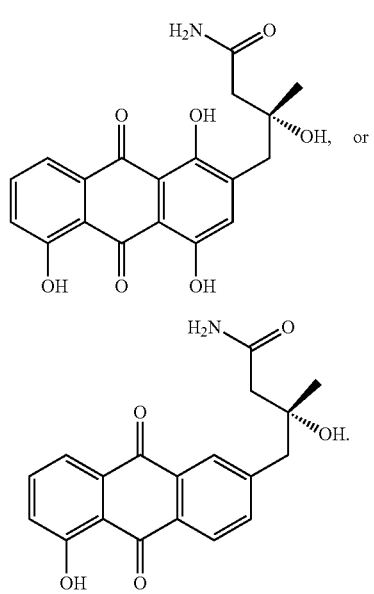

The invention claimed is:

1. A compound of formula 1 or formula 2

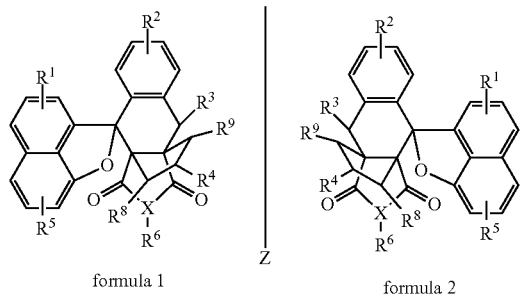

formula 1    formula 2 wherein X can be an N, O or S atom wherein $R^1$, $R^2$, $R^3$, $R^4$, $R^5$, $R^8$ and $R^9$ are each independently aryl, acyl, methyl, $C_2$-$C_{10}$ alkyl, $C_3$-$C_6$ cycloalkyl, monosaccharide, polysaccharide with 2-5 consecutive saccharide rings, O, OH, N, NH, S, SH, hydrogen or an ether of the general formula —O—$R^7$, wherein $R^7$ is methyl, ethyl or propyl; and $R^6$ is aryl, acyl, methyl, $C_2$-$C_{10}$ alkyl, $C_3$-$C_6$ cycloalkyl, monosaccharide, polysaccharide with 2-5 consecutive saccharide rings, O, OH, or hydrogen.

2. The compound according to claim 1 of formula 3 or 4

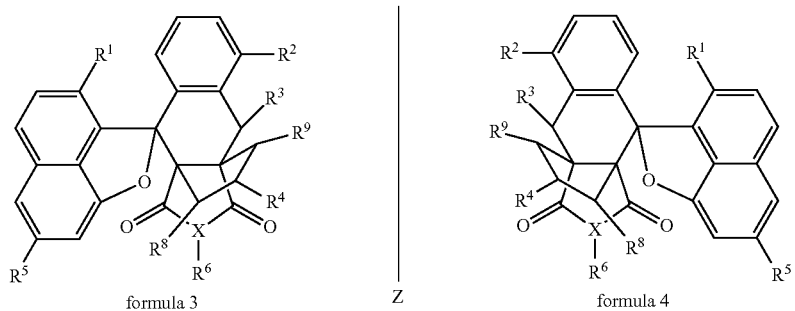

formula 3    formula 4 wherein X can be an N, O or S atom.

3. The compound according to claim 1 wherein $R^1$, $R^3$ and $R^4$ are —OH; $R^2$ is —O—$CH_3$; $R^5$ is $CH_3$; and $R^6$ is hydrogen.

4. A composition comprising at least two compounds according to claim 1, wherein one of said compounds is a compound of formula 1 and another of said compounds is a compound of formula 2.

5. A method for inhibiting growth of a micro-organism, cell or virus comprising culturing the micro-organism, the cell or the virus in the presence of an effective amount of a compound according to claim 1.

6. A method for producing a compound according to claim 1, comprising culturing a *Streptomyces* bacterium characterized in that the bacterium is of the strain deposited at the CBS under deposit number 138593.

7. The method of claim 6, further comprising harvesting the compound.

8. A method for inhibiting the growth of a bacterium, a fungus or a eukaryotic cell comprising culturing the bacterium, the fungus or the eukaryotic cell in the presence of a growth inhibiting amount of a compound according to claim 1.

9. A compound of the following:

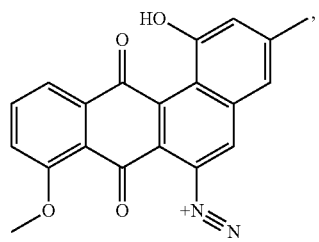

5

-continued

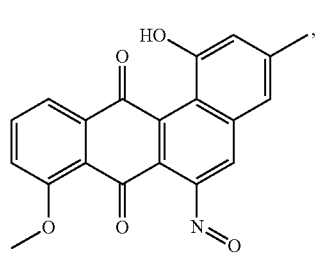

6